US010352921B2

(12) United States Patent
Singhal

(10) Patent No.: US 10,352,921 B2
(45) Date of Patent: Jul. 16, 2019

(54) INTEGRATED BLOOD GLUCOSE MEASURING DEVICE WITH A TEST STRIP PACKAGING SYSTEM

(76) Inventor: Tara Chand Singhal, Torrance, CA (US)

( * ) Notice: Subject to any disclaimer, the term of this patent is extended or adjusted under 35 U.S.C. 154(b) by 751 days.

(21) Appl. No.: 13/374,494

(22) Filed: Dec. 30, 2011

(65) Prior Publication Data

US 2012/0305419 A1    Dec. 6, 2012

Related U.S. Application Data

(63) Continuation-in-part of application No. 13/134,148, filed on May 31, 2011, now Pat. No. 9,924,892.

(51) Int. Cl.
*A61B 5/15* (2006.01)
*A61B 5/157* (2006.01)
*G01N 33/487* (2006.01)

(52) U.S. Cl.
CPC ........ *G01N 33/48757* (2013.01); *A61B 5/157* (2013.01); *A61B 5/150358* (2013.01); *A61B 2562/0295* (2013.01); *G01N 33/48778* (2013.01)

(58) Field of Classification Search
CPC ....... G01N 33/48757; G01N 33/54386; G01N 2035/00089; G01N 33/4875; A61B 5/14532; A61B 2562/0295
USPC ......................................... 600/573, 583, 584
See application file for complete search history.

(56) References Cited

U.S. PATENT DOCUMENTS 3,759,378 A *  9/1973  Werth ................ B65D 21/0205
                                                    206/192
3,872,968 A *  3/1975  Hawkins ................ B65D 85/04
                                                    206/278
5,971,941 A * 10/1999  Simons et al. ................ 600/573
6,036,924 A *  3/2000  Simons et al. ................ 600/583
6,472,220 B1* 10/2002  Simons et al. .................. 436/63
6,872,358 B2*  3/2005  Hagen .............. G01N 33/48757
                                                    422/430
6,881,578 B2*  4/2005  Otake .............. G01N 33/48757
                                                    204/403.02

(Continued)

FOREIGN PATENT DOCUMENTS

EP        1352611 A1 * 10/2003    ....... G01N 33/48757
EP      1 362 551 A1    11/2003
EP        1854738 A2 * 11/2007    ......... B65D 83/0829

OTHER PUBLICATIONS

PCT Partial Search Report PCT/US2012/034011 dated Jul. 4, 2012, pp. 4 and 5.

*Primary Examiner* — Sean P Dougherty
(74) *Attorney, Agent, or Firm* — Steve Roeder, Esq.

(57) ABSTRACT

An integrated blood glucose measuring device is described that has blood glucose metering device, a glucose metering test strip storage mechanism attachable to the metering device, a test strip feeding mechanism for feeding a single test strip from the storage mechanism for blood intake. The metering device, the test strip storage mechanism and the test strip feeding mechanism are integrated into a single device for blood glucose measurement. In another embodiment, a lancet mechanism is attachable to a side of the metering device and thus the metering device, the storage mechanism, the test strip feeding mechanism, and the lancet mechanism are integrated into a single device for blood glucose measurement.

17 Claims, 15 Drawing Sheets

(56) References Cited

U.S. PATENT DOCUMENTS

| | | | |
|---|---|---|---|
| 6,908,008 B2* | 6/2005 | Pugh | 221/135 |
| 7,582,262 B2* | 9/2009 | Funke et al. | 422/430 |
| 2002/0076349 A1* | 6/2002 | Aitken | G01N 33/48757 422/430 |
| 2003/0116583 A1* | 6/2003 | Pugh | 221/268 |
| 2005/0143675 A1 | 6/2005 | Neel | |
| 2005/0281706 A1* | 12/2005 | Funke et al. | 422/63 |
| 2006/0182656 A1* | 8/2006 | Funke et al. | 422/58 |
| 2007/0173739 A1 | 7/2007 | Chan | |
| 2007/0173740 A1* | 7/2007 | Chan et al. | 600/583 |
| 2008/0190766 A1* | 8/2008 | Rush | A61B 5/1411 204/400 |
| 2008/0217353 A1* | 9/2008 | Newman et al. | 221/210 |
| 2008/0299009 A1* | 12/2008 | Angelides | 422/82.01 |
| 2009/0270765 A1* | 10/2009 | Ghesquiere et al. | 600/583 |
| 2009/0277923 A1* | 11/2009 | Funke et al. | 221/154 |
| 2010/0025425 A1* | 2/2010 | Jang | G01N 33/48757 221/277 |
| 2010/0051455 A1* | 3/2010 | Wooldridge | B01L 3/5023 204/403.01 |
| 2011/0210021 A1* | 9/2011 | Logel | G01N 33/48778 206/223 |
| 2011/0226643 A1* | 9/2011 | Kates | A61B 5/14532 206/305 |
| 2011/0278321 A1* | 11/2011 | Chan | A61B 5/14532 221/198 |
| 2012/0199601 A1* | 8/2012 | Sawa | G01N 33/48757 221/1 |
| 2012/0310114 A1* | 12/2012 | Singhal | A61B 5/14532 600/583 |

\* cited by examiner

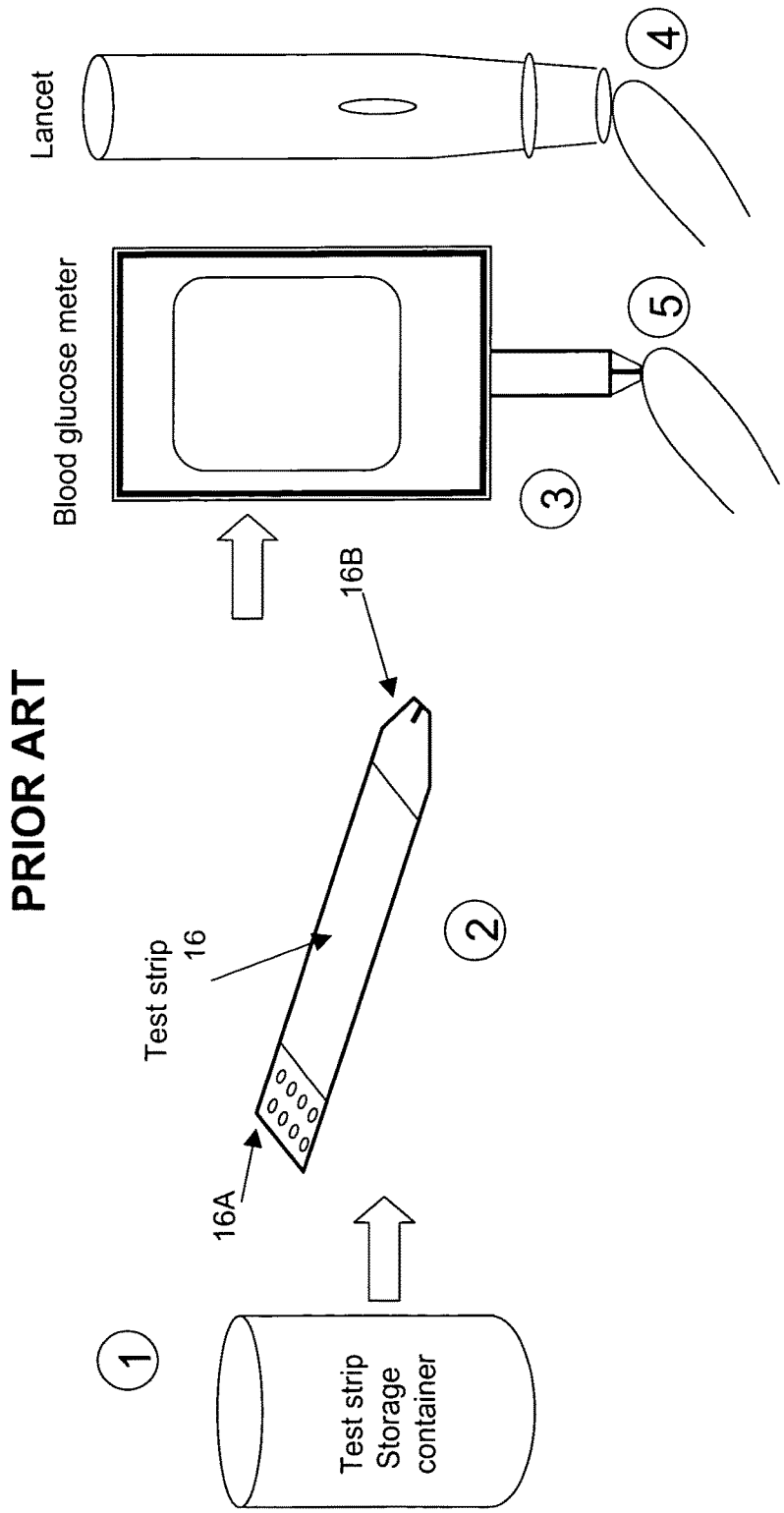

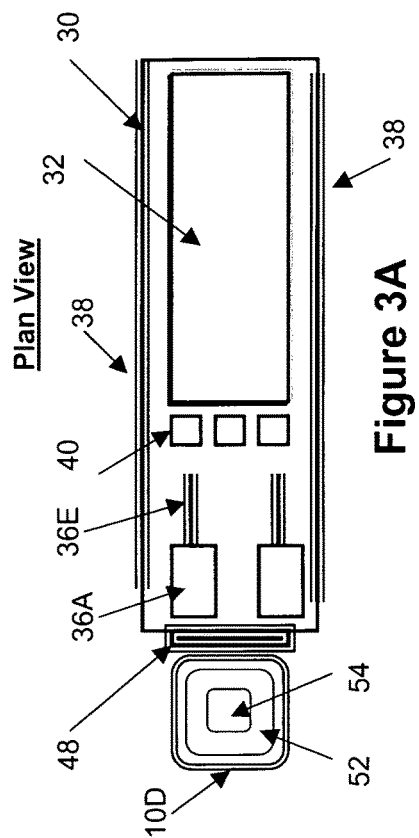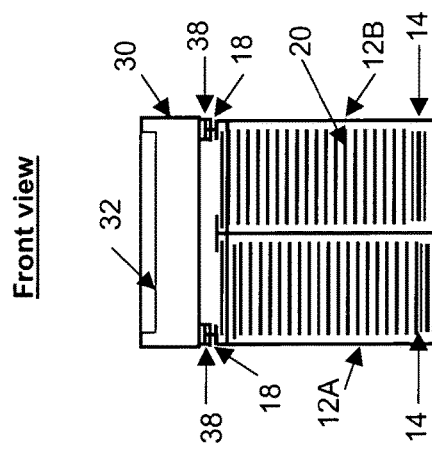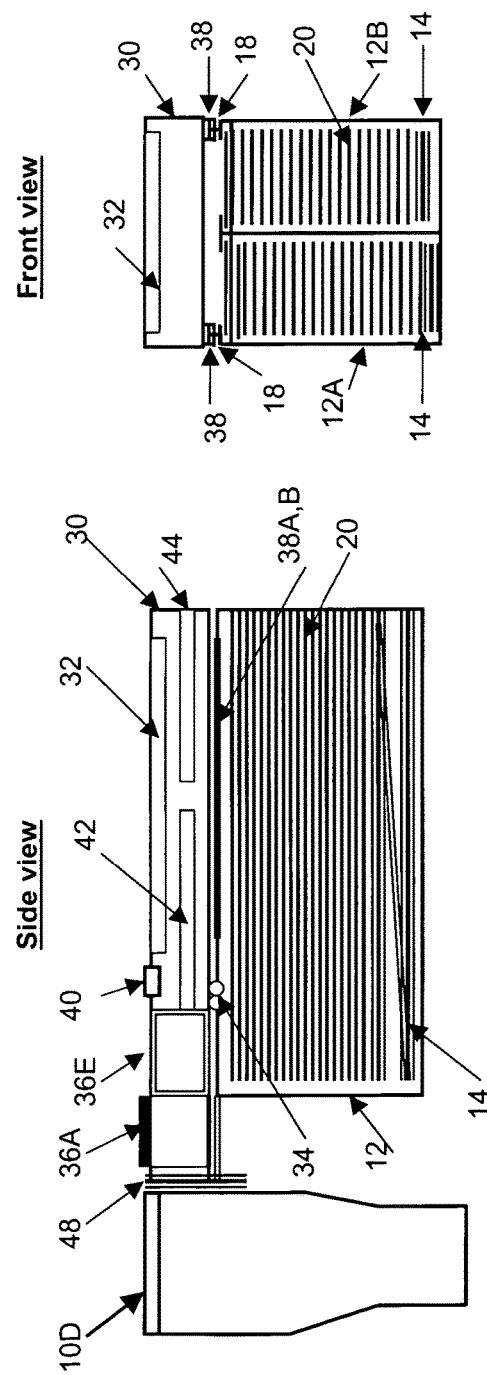

At step 100, integrating a test strip storage magazine with a blood glucose meter At step 102, integrating a test strip feed mechanism from the storage magazine with the blood glucose meter At step 104, integrating a lancet mechanism with the blood glucose meter At step 106, enabling releasing a test strip and automatically activating meter, when strip connects to meter contacts At step 108, enabling using the deployed strip for blood intake from the finger At step 110, enabling reading a glucose value from the meter At step 112, enabling activating a meter switch to display a graph with the current reading At step 114, enabling inserting a test strip storage magazine into the meter At step 116, enabling removing and replacing a used magazine with a new magazine At step 118, integrating a dual test strip feed mechanism from the dual storage magazine for use with the meter

Figure 4

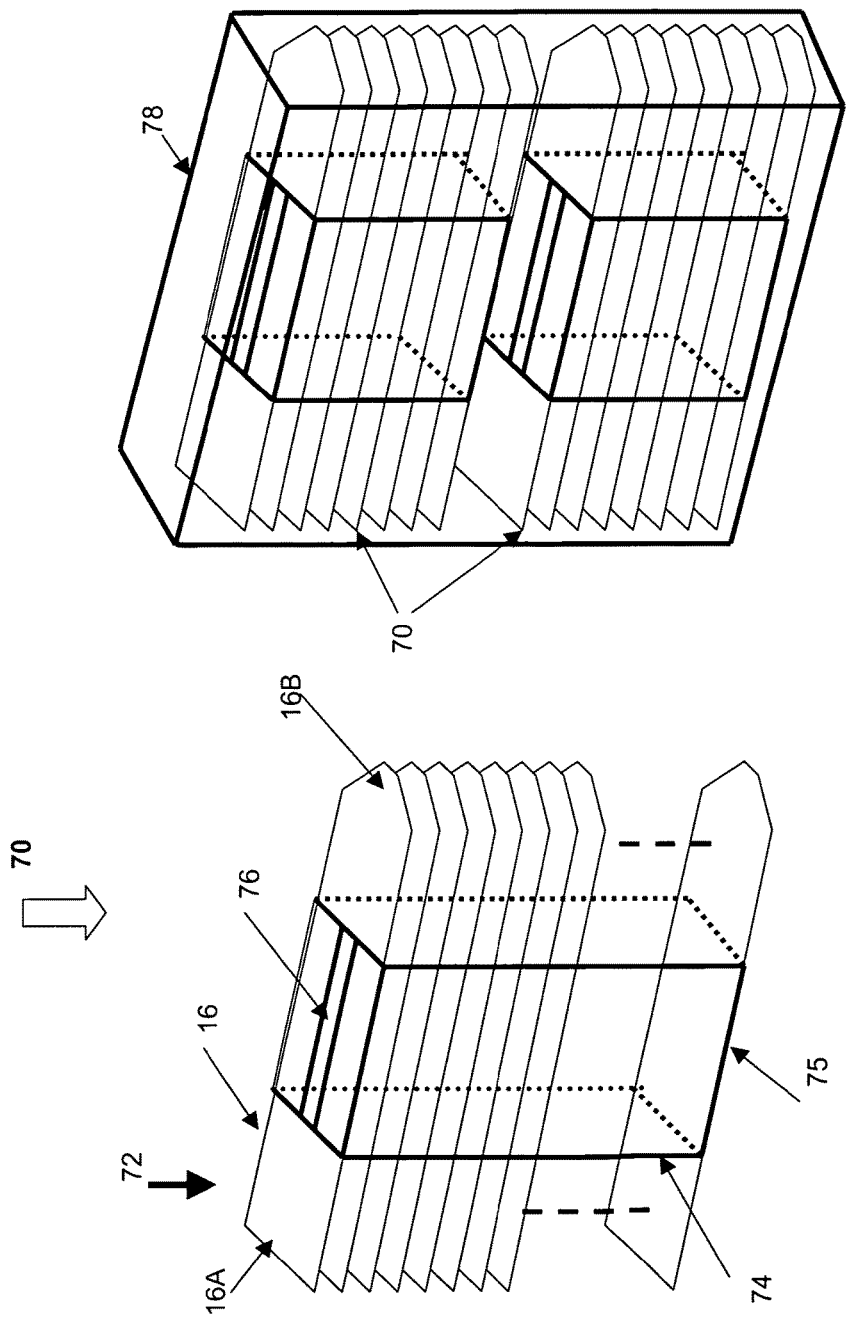

At step 120, stacking the test strips on top of each other in a stack with each strip aligned in the same orientation of the ends within the stack; and At step 122, the stack held together by a removable strip wrapper.

At step 124, packing the strips in the stack with one of 20, 25, 30, 35, 40, or 50 strips in one stack.

At step 126, storing the stack in an air tight container for removal there from for inserting the stack in a test strip magazine for use with a blood glucose meter.

At step 128, enabling removal of the stack from the air tight container, enabling insertion of the stack in a test strip magazine and enabling removal of the strip wrapper, enabling use of the stack of test strips with a blood glucose meter.

At step 130, sizing the container to hold multiple stacks.

Figure 6C

Test Strip Pack Batch Code & RFID Logic 85

1. Place a new Test Strip Pack near the RFID adapted meter and manually activate on the meter, a new test strip batch function.
2. The RFID logic in the meter reads the RFID tag.
3. The RFID logic 85 parses the Qty. and batch code and store in the meter memory.
4. The logic copies the qty to qty. logic and the code to the code logic.
5. A new test strip is used/inserted in the meter from the magazine.
6. The test logic uses the stored code.
7. If the test strip is of the type that has the code on the test strip itself, the logic compares the two codes and verifies that the codes match.

Figure 7C

At step 132, operating by a meter logic the meter functions including that of (i) sensing insertion of strip, (ii) sensing intake of blood sample and (iii) yields a measurement.

At step 134, having a test strip count logic and a test strip count display in the meter.

At step 136, adapting the meter logic to send a signal, when one or more of the meter functions are sensed, to the count logic.

At step 138, receiving the signal by the count logic, and maintaining a strip use count in the count logic and displaying by the count logic the test strip use count using the count display on the meter.

At step 140, maintaining by the count logic two count values, one for the test strip stock quantity at hand with a user, and the other count for either how many strips have been used or remain from the stock quantity.

At step 142, displaying by the count logic on the count display side by side, the stock count value and the use count value.

At step 144, computing by the count logic a remainder stock value, each time a count use value is updated and if the remainder falls below a threshold, the count logic via the count display annunciates a legend "order new stock", or annunciates an alternate flashing display with count values and "order new stock" legend.

At step 146, annunciating the display each time the meter is used with a test strip or just powered-up.

At step 148, initializing a stock value with a standard quantity of the package from a list of 25, 50, 100, 200, and 300.

Figure 8A

At step 150, adapting the meter with a low power RFID transmitter receiver logic limited to operate within a distance of less than a foot;

At step 152, operating manually the RFID logic once when a new stock of test strips is received and placed in the close vicinity of the meter and the logic reads the RFID tag on the stock supply to automatically read and update the stock count value in the count logic.

At step 154, attaching an RFID tag with a tag number to the package, the number in the tag corresponds to the quantity of test strips in the package.

At step 156, making the number in the tag in addition corresponds to a batch number of the test strips and calibration coefficients for the batch.

At step 158, making the RFID tag removable from the package, when the tag number has been read by a meter equipped with the RFID logic.

At step 160, placing the RFID tag on a flap of the test strip package and the flap is removed to remove the RFID tag, when the tag number has been read by a meter equipped with the RFID logic.

At step 162, sizing the RFID transmit energy to transmit a distance less than a foot from the receiver.

Figure 8B

INTEGRATED BLOOD GLUCOSE MEASURING DEVICE WITH A TEST STRIP PACKAGING SYSTEM

CROSS REFERENCE

This application claims priority from and is a continuation-in-part (CIP) of application Ser. No. 13/134,148, filed May 31, 2011, now U.S. Pat. No. 9,924,892 titled 'Integrated Blood Glucose Measuring Device" of Tara Chand Singhal.

A companion application that claims priority from and is a second continuation-in-part (CIP) of application Ser. No. 13/134,148, filed May 31, 2011, the companion application titled "An Integrated Blood Glucose Measuring Device with a Test Strip Count System" is being filed on the same date as this application.

FIELD OF THE INVENTION

The packaging of test strips for use in a test strip magazine and a test strip magazine for use with a blood glucose meter are described.

BACKGROUND

People across the United States and around the world suffer from a metabolic disease called diabetes. For these people who suffer from diabetes and are injecting insulin, a blood glucose meter is used at home to monitor their blood glucose levels. The blood glucose level in their blood is measured and monitored at different times of the day on a regular basis. The blood glucose meter works with a test strip and a lancet.

At the time of the blood glucose measurement, a test strip is retrieved from a storage container. The test strip is about ⅜" wide and 1.5 inch long. The test strip has an electrical interface-end and a blood intake-end. The electrical interface-end of the test strip is inserted in the meter to activate the meter. The lancet is then used to prick the finger and draw a droplet of blood. The blood intake-end of the test strip sticking out of the meter is then touched to the finger for blood intake into the test strip. The meter, after a processing delay, provides a blood glucose reading in a display screen of the meter. The meter has logic to retain multiple readings and display them on demand and also transfer them to a computer for analysis.

There are about half a dozen companies that make blood glucose meters for use in both the home settings and in hospitals. These companies are Abbott Laboratories, Bayer Health Care, Life Scan, Roche, Nipro, Arkray, and Aga Matrix. These companies market many popular brands of blood glucose meters in different form-factors. These companies also market the tests test strips that fit their meters and the lancets.

Typically, a blood glucose meter is 2 inches by 3 inches and ½ an inch thick in size. A lancet is like a pen like device about 5 inch long and around ½ an inch in diameter. The improvements by the industry in the prior art as described above have been to reduce the form-factor size of the meter device as well as improve the accuracy of the measurement. However, as illustrated in the Prior Art FIG. 1, the number of items and the steps required to measure the blood glucose levels have stayed the same.

It is the objective of the embodiments herein to make possible an integrated blood glucose measurement device that reduces the number of items a user would have to carry. It is also the objective to reduce the number of steps a user would have to perform and also to reduce the overall size of such an integrated blood glucose measurement device to make it easier to carry and use.

SUMMARY

An integrated blood glucose measuring device is described. The integrated device has blood glucose metering device, a test strip storage mechanism attachable to the metering device, and a test strip feeding mechanism for feeding a single test strip from the storage mechanism to the metering device ready for blood intake. The metering device, the test strip storage mechanism and the test strip feeding mechanism are integrated into a single device for blood glucose measurement.

In another embodiment, a lancet mechanism is attachable to a side of the metering device and thus the metering device, the test strip storage mechanism, the test strip feeding mechanism, and the lancet mechanism are integrated into a single device for blood glucose measurement.

The test strip storage mechanism may have dual compartments for storing a dual stack of measurement test strips for enhanced storage capacity. Each compartment is sized to hold a stack of test strips. Each compartment has a spring device at the bottom of the compartment that pushes the test strips up to an area with guides at the top of the compartment that hold a top test strip in place for retrieval. The test strip storage mechanism is similar in some aspects to that as used in an ammunition magazine. In an ammunition magazine cylindrical shape bullets are stored that are pushed up into a firing chamber via a spring. In the embodiments described herein of the test strip storage mechanism, test strips that are flat and rectangular pieces of plastic are stored and are pushed up in position by a spring.

These and other aspects of the embodiments herein are further described in detail with the help of the accompanying drawings and the description, where similar numbers are used to identify the features of the embodiments.

BRIEF DESCRIPTION OF THE DRAWINGS

Some of the novel features of the embodiments will be best understood from the accompanying drawings, taken in conjunction with the accompanying description, in which similar reference characters refer to similar parts, and in which:

FIG. 1 shows block diagrams that illustrate features of the prior art for blood glucose measurement.

FIGS. 3A-C are plan, side and elevation views respectively of a preferred embodiment of a glucose measurement device.

FIG. 4 is a method diagram that illustrates features of a preferred embodiment of the glucose measurement device.

FIGS. 6A-6B are block diagrams that illustrate features of a preferred embodiment of test strip packaging for a magazine of the embodiments herein.

FIG. 6C is a method diagram that illustrates features of a preferred embodiment of the package of test strips and their use in a magazine.

FIGS. 7A-7C are block diagrams that illustrates features of a preferred embodiment meter with a test strip count and a batch code RFID system.

FIGS. 8A-8B are method diagrams that illustrate features of a preferred embodiment a meter with a test strip count and a batch code RFID system.

DESCRIPTION

Introduction

As illustrated in Prior Art FIG. 1, to measure blood glucose, at step 1, a test strip 16 is retrieved from a storage container. The test strip 16 has an electrical interface-end 16A and a blood intake-end 16B. At step 2, the electrical interface-end of the test strip is inserted into a meter with the blood intake-end sticking out. At step 3, the meter senses the test strip and provides ready indication in the display window. A user then at step 4, uses a lancet to draw blood from a finger and at step 5, uses the finger with the blood to touch to the test strip. After a processing delay, the meter provides a reading of the blood glucose.

In prior art, this regimen of using a blood glucose meter is required and is repeated multiple times in a day. These blood glucose measuring items, test strips in a storage container, the meter, and the lancet need to be carried with the user. The embodiments described herein provide improvements by integrating these different items into a single compact blood glucose measuring device, that reduces the number of items as well as the steps as described above in the prior art.

Figure 2A:
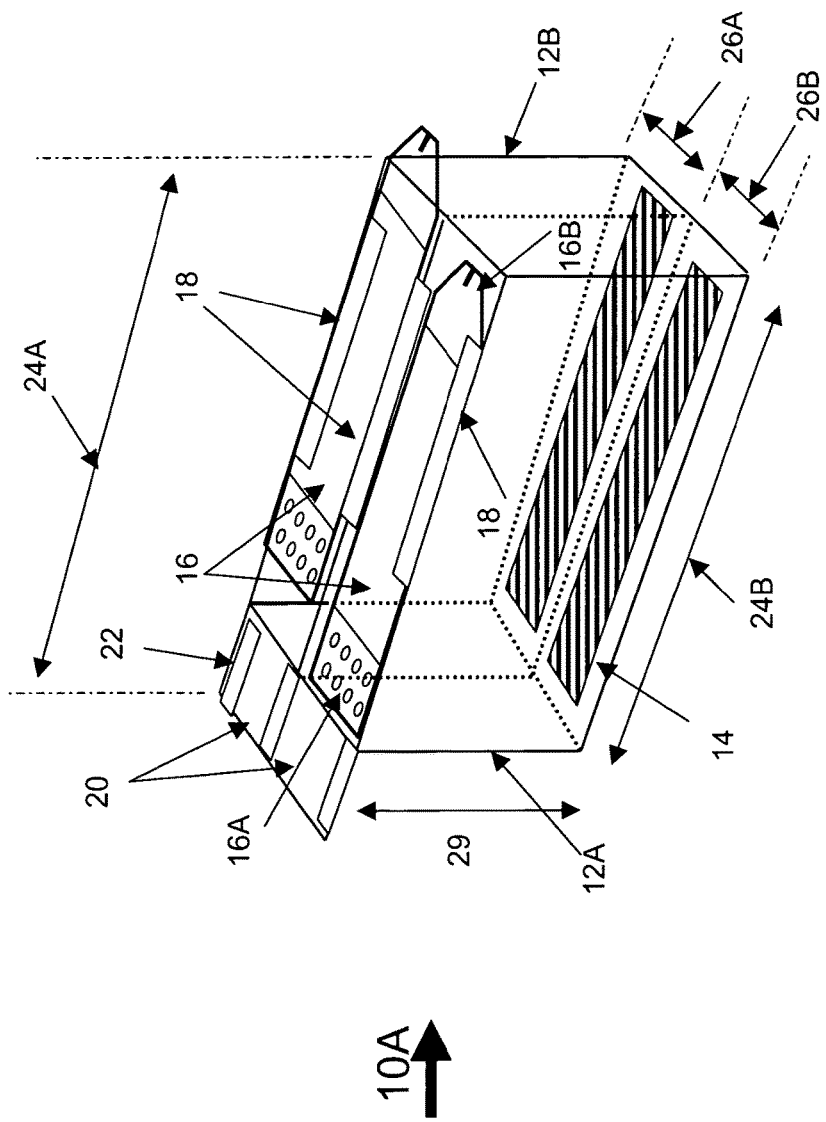
FIG. 2A is a block diagram that illustrates features of a preferred embodiment of a test strip storage magazine.

As shown in FIGS. 2A, 2B, 2C and 2D, there are different embodiments that are described. As shown in FIG. 2A, there is a test strip storage device 10A, that is used as a storage chamber for the test strips.

Figure 2B:
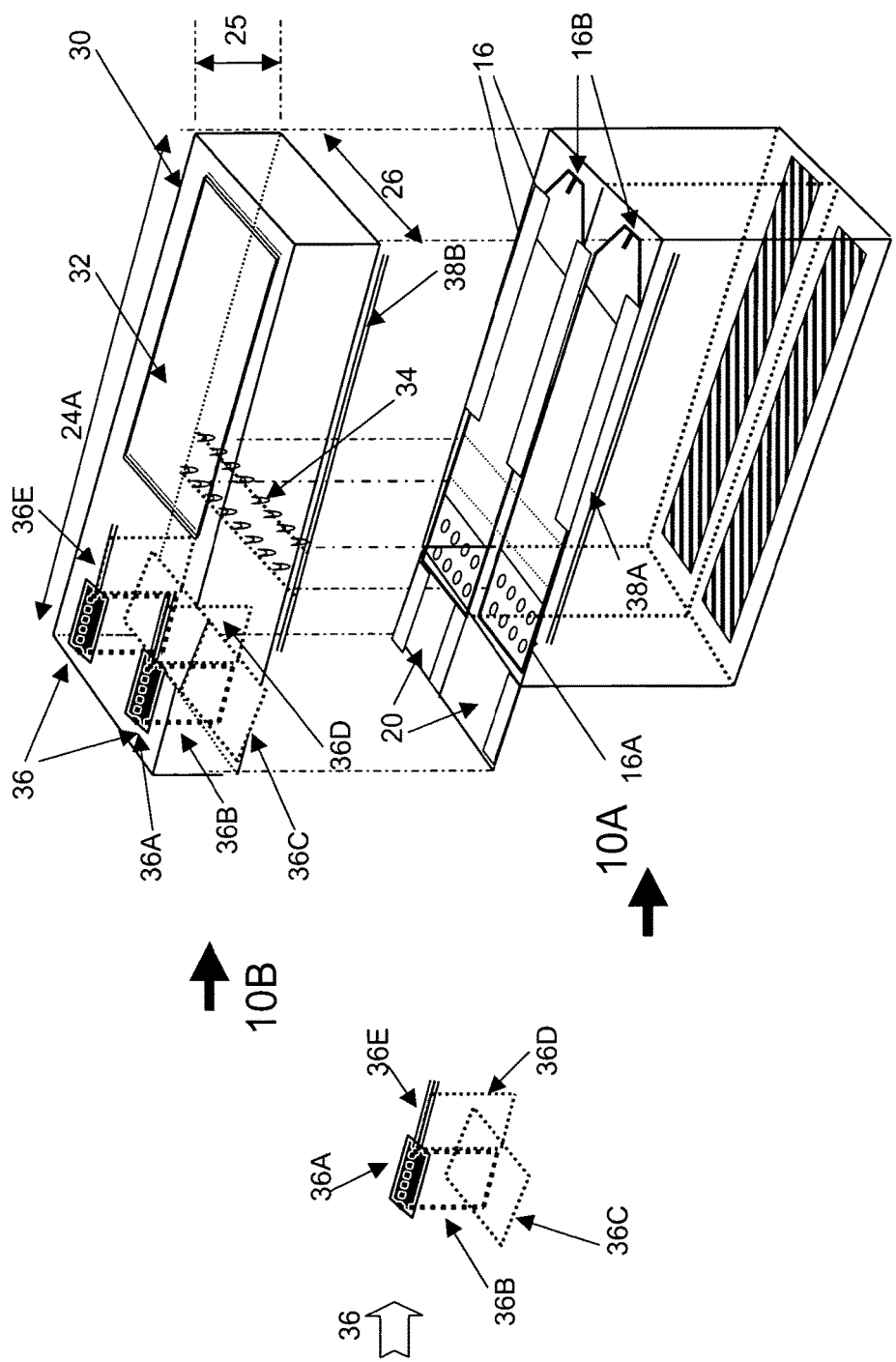
FIG. 2B is a block diagram that illustrates features of a preferred embodiment of integrating a test strip storage magazine with a meter.

As shown in FIG. 2B, a metering device 10B is attached to the storage device 10A. In this embodiment the test strips from the test strip storage 10A are automatically inserted into the meter 10B and the test strip is automatically electrically interfaced to the meter device.

Figure 2C:
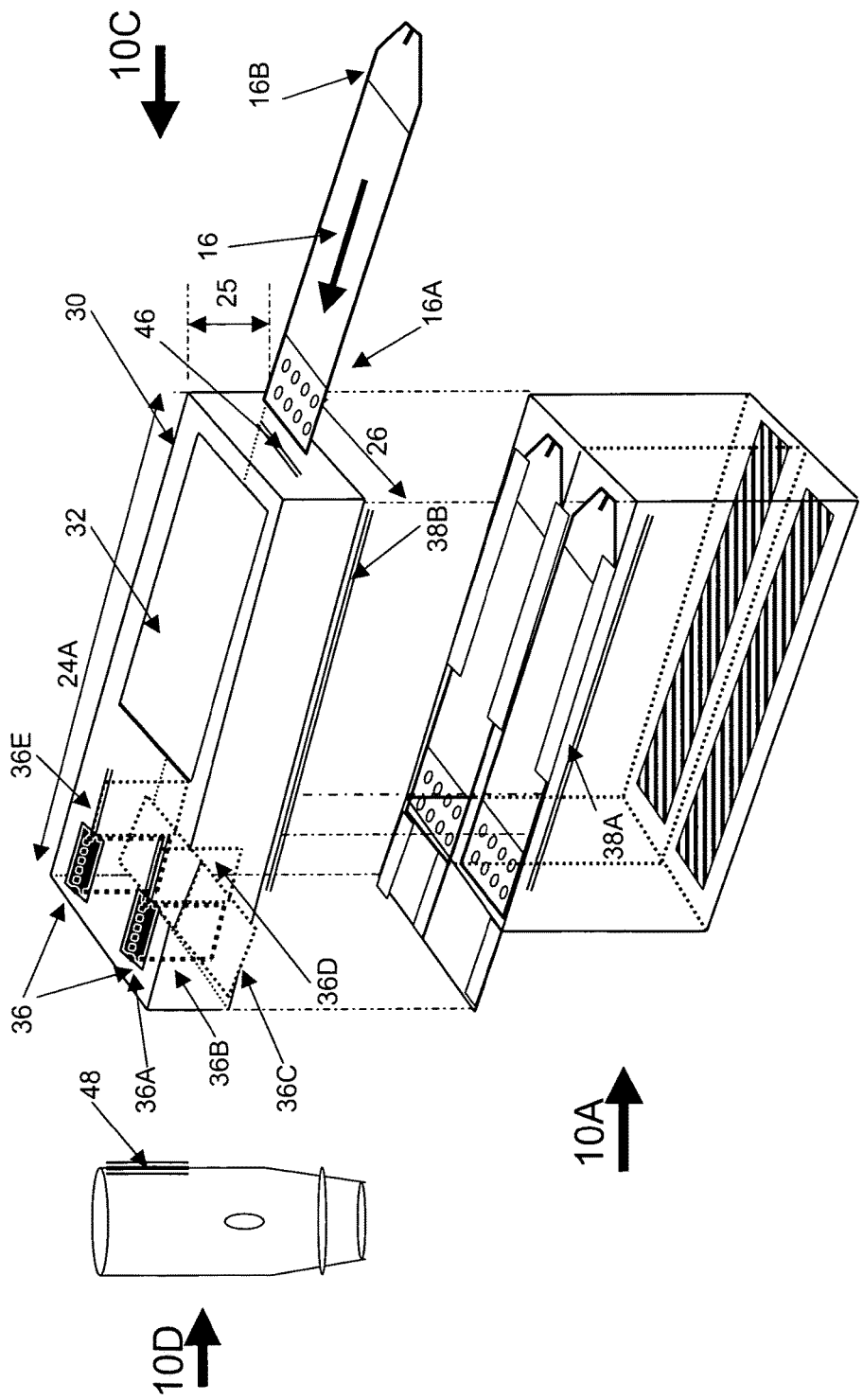
FIG. 2C is a block diagram that illustrates features of another embodiment of integrating a test strip storage magazine with a meter.

As shown in FIG. 2C, a metering device 10C is attached to the storage device 10A. In this embodiment, the test strip is retrieved from the storage device 10A and is then manually inserted into the meter device 10C.

Figure 2D:
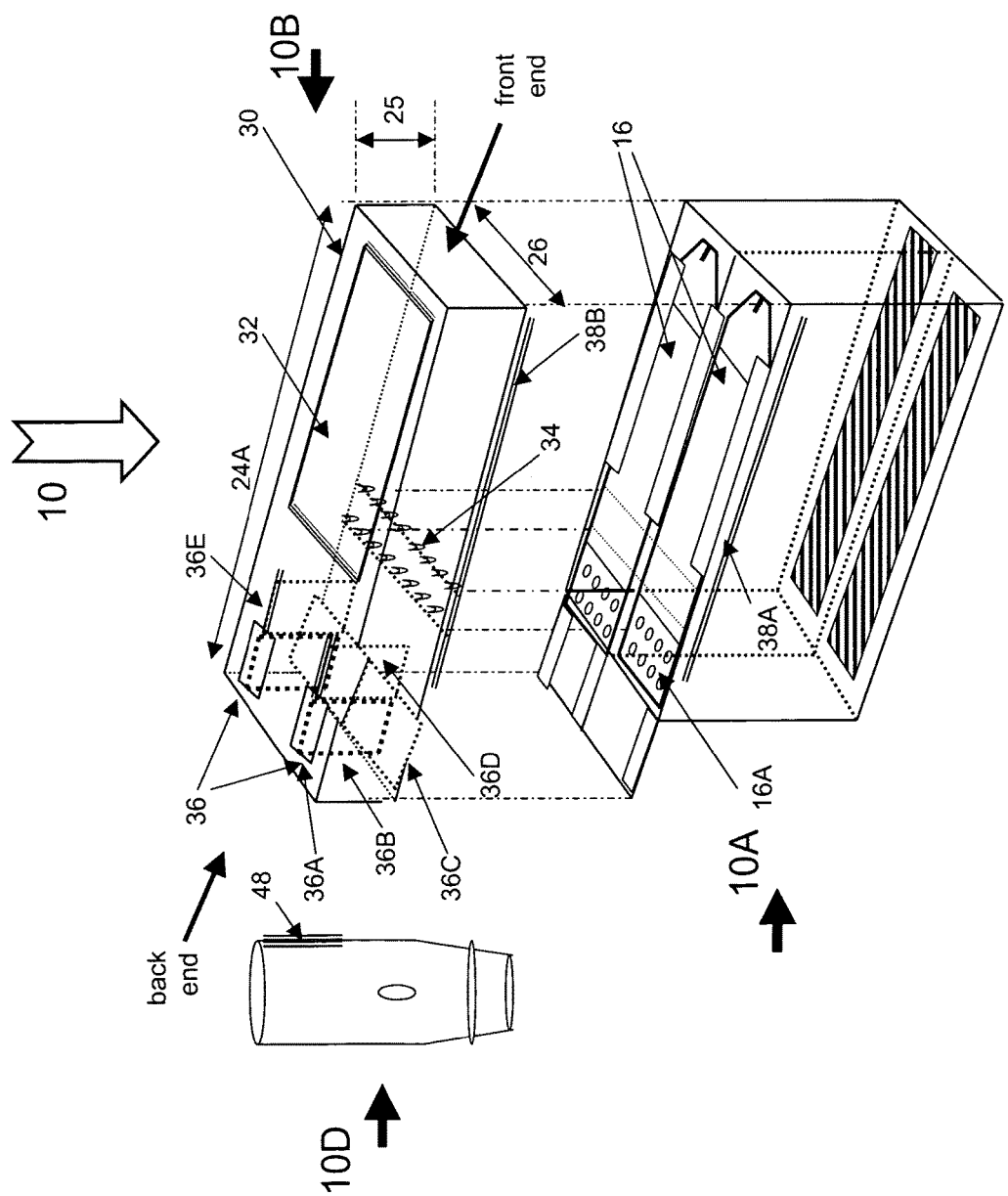
FIG. 2D is a block diagram that illustrates features of a preferred embodiment of integrating a test strip storage magazine with a metering device and a lancet mechanism.

As shown in FIG. 2D, a lancet device 10D may also be attached to the meter 10B. A lancet device 10D may also be attached to meter device 10C in FIG. 2C.

In one embodiment, as shown in FIG. 2B, the test strip storage devices 10A and meter device 10B are integrated into a single device. In another embodiment, as shown in FIGS. 2C and 2D, all three devices, test strip storage device 10A, the meter device 10B or 10C, and the lancet device 10D are integrated in a single unit. In an alternative embodiment, as shown in FIG. 2C, the test strip is manually inserted into the meter device 100, whereas, in the embodiment as in FIG. 2B, the test strip is automatically inserted into the meter.

Test Strip Storage Magazine 10A

As illustrated in FIG. 2A, the storage device 10A, has a left storage magazine 12A and a right storage magazine 12B positioned side by side and attached to each other. They are a single unit with two side by side or dual magazines. Each of the chambers 12A and 12B has a separate spring mechanism 14 at the bottom of the chamber. Each of the chambers 12A and 12B may be individually stacked with test strips 16. The interface-end 16A of the test strip 16 is on one end and the blood intake-end 16B on the other end of the chamber. On the top of the chambers 12A and 12B, there are positioned guides 18 that keep the top test strip of the stack in place and are used to guide the movement of the test strip as the test strip is pushed at the test strip end 16A. These guides may be built as integral to the chambers 12A and 12B and as part of one fabrication or molding process. There are three guides 18, two on the outer walls of the chambers 12A and 12B and one on the middle wall between the chambers that is used for both these chambers, as the two chambers 12A and 12B have a one common wall or partition in the middle.

At the left end of the chambers, there is provided a platform 20 with its own guides 22 for the two chambers 12A and 12B. This platform 20 and the guides 22 are used to provide space for a push plate 36C of a test strip feed mechanism 36 as shown and described later with the help of FIG. 2B.

As shown in FIG. 2B, the dual magazine 10A has guides 38A, one on each side of the magazine and corresponding guides 38B, one on each side of the meter 10B. These guides 38A and 38B enable the magazine 10A to be slid on to the bottom side of the meter 10B and securely attached to the meter with the help of guides 38A and 38B.

The magazine 10A may be made of any suitable plastic material that may be a clear or see through material and allows a user to visually see the stack of the test strips in each of the compartments 12A and 12B and to also see how many test strips are left in the magazine and which one of these two magazines is nearly empty. Alternatively or in addition, as described later, a test strip count system may display on a display window of the meter 10B how many strips have been used or remain in the magazine 10A.

Alternatively, the magazine may be made of opaque material, and the quantity of the test strips in the magazine may be indicated by a count on the meter display. As each test strip is inserted into the meter a count may be kept, decremented, and displayed on the display 32 of the meter body 30.

All dimensions and sizes described herein are notional and approximations. A typical capacity of the magazine is likely to be 64 in number, 32 in each compartment. This capacity is based on the assumption that a test strip 16 is likely to be 1/32 inch thick and the magazine 10A is likely to be 1¼ inch in height allowing for a ¼ inch space for the positioning of the spring in the magazine. Thus a one inch vertical space in the magazine would store 32 test strips in each compartment and dual magazine would store 64 test strips. However, the magazine may be sized to store 100 test strips by increasing the vertical space in the magazine.

The magazine 10A may have a detachable lid or a compartment cover in the form of a lid at the bottom of the magazine (not shown). The lid may be detached or removed to insert a stack of test strips and the lid may have a spring mechanism in the lid itself enabling the magazine to be filled in with test strips and closed from the bottom of the magazine. Alternatively, the magazine 10A may be filled in from the top one test strip at a time.

If the magazine is sold as a replacement magazine, then the magazine may come with a pre-stored supply of test strips and the magazine is discarded when it is empty and new magazine used and inserted with the help of guides 38A and 38B into the meter body 30.

If the magazine 10A is sold as already integrated with the meter 10B, then a second method may be used to refill the magazine. In this method, the test strips that are sold for this purpose may be packed as stacks, enabling two packs of test strips to be dropped in the magazine from the bottom and the lid with the spring pushed in and securely locked in place.

The magazine spring may be similar to what is used in ammunition magazines which pushes up the stack of bullets in the magazine, as each bullet is positioned in the firing chamber. Alternatively, the spring may be of a different design such as a helical coiled spring.

The spring would be attached to and push a platform that is substantially sized to the size of the test strip 16. The platform would then hold and push the stack of test strip inside a chamber of the magazine. Prior art teaches such uses of a spring and a platform to push a stack. On example is that of a stack of paper in a copier machine that rests of a platform that is pushed up by springs. No specific claim is made for such spring based push mechanisms except that which is specifically disclosed for use in the test strip magazine of the embodiments herein. The design of the spring in the embodiments herein enables the last test strip of the stack to be pushed all the way up to the guides 18.

What has been described above is a preferred embodiment of the test strip storage magazine 10A. Many other embodiments may be possible and are not ruled out. One such embodiment may be where the magazine 10A and the meter 10B are arranged upside down and that would enable and allow gravity to feed the test strips into the meter.

Integration of Meter 10B and Test strip Storage Magazine 10A

As shown in FIG. 2B, a meter 10B is shown positioned on top of the storage magazine 10A. The meter 10B has a guide system with guide members 38B on the meter and with guide members 38A on the storage magazine 10A, that enable the magazine 10A to be inserted or slid into the meter 10B to become and function as one integrated unit.

The meter 10B has a meter body 30, with a display window 32 on the top side, electrical contacts 34 on the underside of the body 30, which connect the test strip 16 to the meter when the test strip is pushed forward in position with the help of a feed mechanism 36. There are two individual test strip feed mechanisms for two magazines 12A and 12B respectively.

Test Strip Feed Mechanism 36

With reference to FIG. 2B, a test strip feed mechanism 36 is described. The mechanism 36 has a push member 36A, a vertical member 36B, a slide plate 36C, a spring 36D and a guide groove 36E in the meter body. The push member 36A is positioned on top of the meter body 30 and has a vertical member 36B attached to the push member 36A. The vertical member 36B is attached to a horizontal plate 36C. The horizontal plate 36C is positioned on glides or slides on the plate 20 of the magazine 10A, when the magazine 10A and the meter 10B are integrated as one unit.

A groove 36E on the meter body 30 enables the push member 36A to be moved forward against a spring resistance 36D that enables the push member in the form of a plate 36A and thus the slide plate 36C to automatically return to the original position.

When the push plate 36A is slid forward the plate 36C engages and moves the test strip 16 forward in the storage compartment 12A or 12B, depending on which of the two slides of the test strip feed mechanism 36 is used.

As shown in FIG. 2B, the test strip feed mechanism 36 moves or slides the test strip 16 forward a fixed predetermined distance, until the test strip's electrical interface-end 16A make electrical contact with electrical contacts 34 positioned on the underside of the meter body 30. At that position of the test strip 16, in the magazine 10A, the blood intake-end 16B of the test strip 16 extends out of the magazine body by a distance that enables the end 16B to be used for blood intake.

The test strip feed mechanism 36 may be of a different design than what is described above and other designs are not ruled out. For example, the two push members 36A for two magazines may be positioned on the side of the meter body 30 as opposed to on the top as had been described above. The test strip feed mechanism 36 is preferably used by a thumb as the integrated device with meter 10B and the magazine 10A is held in the palm of the hand.

The Meter Body 30

The contacts 34 at the underside of the meter body 30 are dual series of contacts, one set of contacts for each of the two test strips. The meter 30 senses only one of these contacts to be energized depending upon which one of the test strips is used from the magazine. The contacts 34 are spring loaded and permit the sliding of the test strip 16, while at the same time make electrical contact between the meter 30 and the test strip 16. Thus, the contacts 34 make electrical contact with only one test strip interface-end 16A at one time. If by mistake, both sets of contacts are energized then the meter would indicate a fault.

The meter body 30 is sized to be approx. one inch wide 26, half-an-inch high 25 and about two inches long 24A. The meter body 30 sits on top and is attached onto the magazine 10A. The magazine 10A thickness may be sized to be ⅜" plus ⅜" plus a slack margin plus thicknesses of the three wall of the magazine. This thickness of the magazine may equal ⅞". An additional ⅛ inch may be used for guides 38 with two members 38A on the magazine and member 38B on the meter body, thus enabling the width 26 of the meter body 30 and the storage magazine 10A to be the same and thus an overall width of the integrated device to be one inch wide 26. However, the width of the meter 30 and the magazine 10A may be different than these sizes and may be different from each other.

As shown in FIG. 2A, the test strips 16 may be 1.5 inch long and ⅜" wide. The length of the plate 20 to accommodate the slide member 36C may be ½", thus making the length 24A of the magazine 10A to be approximately two inches long. As shown in FIG. 2B, thus, length 24A of the meter body 30 attached to the top of the storage magazine 10A may also be 2" long. However, the size of the meter body 30 may be different then these dimensions.

There is a clearance space between the test strip magazine 10A and the meter 10B, when the two are attached to each other as had been described above. This clearance space accommodates the electrical connections 34 of the meter body 30 and their movement on top of the test strip, as the test strip is pushed out from inside the magazine 10A. This clearance space also accommodates the guides 18 that hold the top test strip in place. This clearance space may be $1/16^{th}$ of an inch and may be as much as $1/8^{th}$ of an inch. The height 25 of the meter body 30 may be ½", thus the height of the integrated device may be close to 2" as well.

Thus the integrated device would have an overall dimension of 2" long, 1" wide 26 and 2" high. Such a integrated device may provide as much as ⅞" by ⅞" display area on the top of the meter body. As shown in plan view FIG. 3A, the meter body 30 may also have three switches 40 on the top side of the meter body 30 to operate different functions of the meter 10B. Prior art enables such small size meters to be fabricated with the modern electronics. An example is the Bayer meter in the approximate form-factor of a USB key.

The orientation of the meter body 30 and the orientation of the test strip storage magazines 12A and 12B, make for convenient alignment and a desirable form-factor. However, the magazine 10A and the meter 10B may be attached to each other in a different orientation of arrangement and such orientations are not ruled out.

Alternatively, the meter body 30 may be made in a size that would be suitable for the embodiments herein. With reference to FIG. 2A, the magazine 10A may be of ¾" wide to accommodate thickness 26A and 26B of two stacks side by side, 1 inch high 29 and 1.5 inch long 24B to accommodate the size of test strips 16 that are ⅜" wide 26A and 26B and 1.5 inch long 24B.

With reference to FIG. 2B, the meter body may be ½ inch high 25, a 1" inch wide 26 and 2 inch long 24A. With reference to FIG. 2D, the lancet 10D may be ¾" square and 1.5" high. Thus the size of an integrated device would be approximately 1" wide, 1.5 inch high and 3 inch long. The quantity of test strips that would be stored in the magazine would be 64 in the two stacks, assuming the thickness of the test strip 16 is increased to ¹/₃₂ inch for the embodiments herein.

Manual Feed of Test Strip into the Meter 10C

As shown in FIG. 2C, in this embodiment, the meter 10C with meter body 30 does not have electrical contacts 34 on the underside of meter body 30 as in embodiment 10B. Instead it has the electrical contacts inside the meter body 30 that are connected to the test strip 16 when the test strip 16 is inserted in the meter body 30 via an opening 46 on the front of body 30. In this embodiment, the test strip 16 is pushed out from the test strip magazine 10A with the help of the test strip feed mechanism 36. The test strip is then manually pulled out and removed from the magazine 10A and then manually inserted in opening 46 on the meter body 30.

Meter 10B Integrated with Test Strip Magazine 10A and Lancet 10D

As shown in FIG. 2D, a lancet mechanism 10D is sized to be attachable to the meter 10B. The lancet mechanism 10D has attachment guides 48 that attach to the backend of the body 30 of the meter 10B.

The prior art lancet mechanism is made in the form-factor of a pen to make it convenient to hold and use. The mechanism in such a lancet may also be made in the form-factor as described in this embodiment. The form-factor of the lancet 10D may be ¾" square and 2 inches long. As shown in FIGS. 3A and 3B, in the plan and side views respectively, such a form-factor lancet 10D would attach to at the back end of the meter body 30. Alternatively the lancet mechanism 10D may also attach (not shown) to the meter body in the front or on the side of the meter body 30.

In some embodiments all the three devices, the test strip magazine 10A, the meter 10B and the lancet mechanism 10D may come pre-built at the factory as one integrated unit. Such a glucose measurement device 10 is shown in FIG. 2D.

The embodiments 10A, 10B, and 10D are further illustrated with the help of a plan view as in FIG. 3A, a side view as in FIG. 3B and a front view as in FIG. 3C. As shown in FIG. 3A, the arm and release mechanisms 52 and 54 of the lancet 10D may be positioned on top of the lancet mechanism 10D.

As illustrated, in the plan view (FIG. 3A), the meter body 30, the display window 32, the attachment mechanism 38 that attaches the meter body 30 with the test strip magazine 10A, the push plate 36A and slide channel 36E of the test strip feed mechanism 36 in the meter body 30, are shown. Further, switches 40 that operate the meter electronics are also shown in their preferred positions. Also shown is a preferred placement of the lancet mechanism 10D that is attached to the meter body 30 via the attachment mechanism 48.

As illustrated, in the side view (FIG. 3B), the meter body 30, the meter display window 32, the switches 40, the meter electronics 42, and the battery 44 are shown. Also shown are the test strip feed mechanism members 36A and 36E. Electrical contacts 34 on the underside of meter body 30 are also shown that make contact with the interface-end 16A of the test strip 16, when the test strip 16 is pushed forward with the help of the test strip feed mechanism 36. The magazine 10A, with a spring 14 at the bottom of the magazine compartment 12 is also shown. Further a stack 20 of test strips 16 is shown and further the mechanism for guide attachment 38 with parts 38A and 38B that attach the magazine 10A to the meter body 30 is also shown.

As illustrated, in the front view (FIG. 3C), the meter body 30, the display window 32, the left and right magazines 12A and 12B respectively with their individual springs 14, and stacks 20 of the test strips 16 are shown. Also the guide 18 for the test strip 16 on the top end of the magazines 12A and 12B are shown. Further the guide 38 that attaches the magazine 10A with the meter body 10B is also shown.

The guides 18 are positioned on top of the magazine with a clearance slightly greater than the thickness of the test strip 16. The test strip 16 thickness is usually $1/64^{th}$ of an inch thick. However, to make the test strip 16 to be easily engaged and pushed forward by the mechanism 36, the test strip 16 thickness may be ¹/₃₂". The test strip 16 has a plastic base on which the test strip parts of electrical conductors and the blood intake gauze are built on. That base thickness of the test strip may be increased without affecting the manufacturing process of the rest of the test strip 16.

The Guide Mechanisms 38 and 48

There are two guide and attachment mechanisms 38 and 48 that are used in the embodiments herein. The guide mechanism 38 is used to attach the storage magazine 10A to the meter 10B. The guide mechanism 48 is used to attach the lancet mechanism 10D to the meter 10B or 10C.

These guide mechanisms may be tongue and groove type providing for a snug fit and attachment between these different assemblies of the integrated glucose measuring device. As a simplified illustration the guide may include a female part of the guide in a U shape channel and the male part of the guide in a T shape channel. The vertical part of the T shape channel is slid into the opening of the U shape channel. The guides may be of another design and such designs are not ruled out.

There is also a locking mechanism that would lock the different devices together. There are many prior art guide and locking mechanisms that may be adapted for use with the embodiments herein. No specific claim is made to any guide and lock mechanism for integrating these separate devices of the meter, the lancet and the test strip magazine.

A blood glucose measuring device has a blood glucose metering device, a glucose metering test strip storage mechanism attached to the metering device, and a test strip feeding mechanism for feeding a single test strip from the storage mechanism directly into the metering device. The metering device, the test strip storage mechanism and the test strip feeding mechanism are integrated into a single device for blood glucose measurement.

The blood glucose measuring device has a lancet mechanism attached to a side of the metering device. The metering device, the storage mechanism, the test strip feeding mechanism, and the lancet mechanism are integrated into a single device for blood glucose measurement.

The storage mechanism uses a rectangular shaped compartment for storage of a stack of test strips. The compartment has a back side and a front side, where a electrical contact side of the test strip is positioned on the back side and a blood intake side is positioned on the front side. The compartment has a bottom side with a spring mechanism for pushing the test strips up and a top side for holding a single test strip for use for blood intake. The top side of the compartment has guides for holding and guiding a single test strip from the stack of test strips, when the feeding mechanism is used to feed the test strip for blood intake.

The storage mechanism has dual compartments for storing a dual stack for enhanced storage capacity, where each compartment is sized to hold multiple test strips in a stack.

The blood glucose metering device, with electrical contacts for a metering test strip, has those electrical contacts positioned on the metering device to make electrical contact with the test strip, when the test strip is extended out of the storage mechanism for blood intake.

The blood glucose measuring device has a feeding mechanism that has a spring loaded lever that pushes a top positioned test strip in the storage chamber forward a distance that enables (i) the test strip's electrical contacts to make electrical contacts with the metering device, and (ii) extend the blood intake side of the test strip out of the storage mechanism for blood intake.

There are two independent feeding mechanisms when the storage mechanism has dual storage compartments, one for each compartment.

The spring loaded lever has a horizontally positioned on a top side of the meter, a slide plate, a slide guide, a vertical member attached to underneath the slide plate, and a horizontal member attached to the vertical member, wherein the horizontal member pushes a single test strip out of the storage mechanism.

The metering test strip is of a thickness that enables the test strip feeding mechanism to engage one test strip at a time for feeding from the storage mechanism.

The lancet mechanism is of dimension in length and girth size that would be attachable to the back side of the metering device and fit within in the contour of the measuring device.

A blood glucose measuring device has a blood glucose metering device, a glucose metering test strip storage mechanism attachable to the metering device, and a manual test strip feeding mechanism for feeding a single test strip from the storage mechanism for blood intake into the meter by manually removing the test strip from the storage and inserting the test strip in the meter, the metering device, the test strip storage mechanism and the test strip feeding mechanism are integrated into a single device for blood glucose measurement.

The blood glucose measuring device has a lancet mechanism attachable to a side of the metering device. The metering device, the storage mechanism, the test strip feeding mechanism, and the lancet mechanism are integrated into a single device for blood glucose measurement.

The storage mechanism uses a rectangular shaped compartment for storage of a stack of test strips. The compartment has a back side and a front side, where a electrical contact side of the test strip is positioned on the back side and a blood intake side is positioned on the front side. The compartment has a bottom side with a spring mechanism for pushing the test strips up and a top side for holding a single test strip for use for blood intake. The top side of the compartment has guides for holding and guiding a single test strip from the stack of test strips, when the feeding mechanism is used to feed the test strip for blood intake.

The storage mechanism has dual compartments for storing a dual stack for enhanced storage capacity, where each compartment is sized to hold multiple test strips in a stack.

Alternative Form-Factor of the Integrated Blood Glucose Meter

The glucose meters are as likely to be used away from home as in the home. Therefore some of the prior art focus has been to make the meter body in a form-factor that makes the meter body relatively small such that it would be easy for the user to carry the meter in their personal possession. An illustrative example of such a small meter body is Bayer® Contour USB, in the form-factor of a USB memory key.

The embodiments described herein earlier have followed that same user driven preference for making the overall integrated meter body smaller that would make the integrated meter easier to carry and use. However, there are different categories of users. These users may be characterized in the categories of male and female and each category may have different preferences regarding the glucose meter form-factor. In prior art, no attempt has been made to make different form-factor meters that are suitable for male and female users and the differences between male and female category meters have been limited to the color of the meter body.

Figure 5:
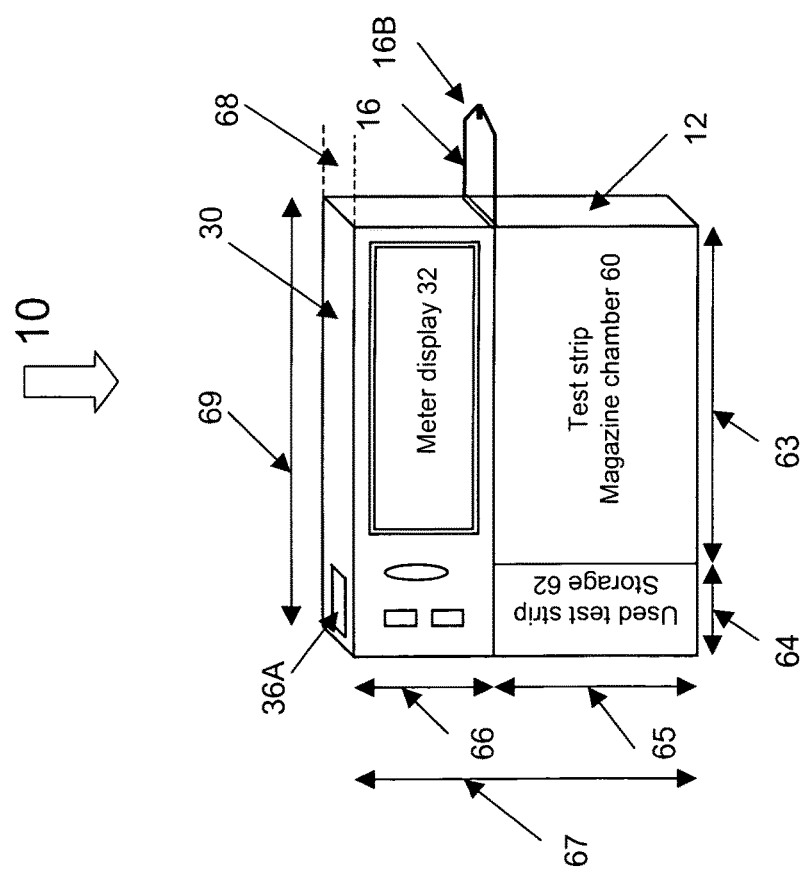
FIG. 5 is a block diagram that illustrates features of a preferred embodiment of alternate form-factor integrated meter and used test strip storage compartment.

As illustrated in FIG. 5, an embodiment of the integrated meter 10 in a slim form-factor that it is believed would appeal to the male gender is described. The male gender is likely to keep the integrated meter body in a pocket on their body, whereas on the other hand, the female gender would likely keep the integrated meter body in their handbag. However, no other limitation is implied or meant in creating the slim integrated meter and it can be used and preferred by any gender or class or category of users and may be made in any desirable color with aesthetic design features.

A new form-factor integrated meter body is illustrated with reference to FIG. 5. This body has a single test strip chamber 60 in the magazine 12 and the meter body 30 is preferably vertically oriented on top of the magazine 12 making for a slim form-factor. This form-factor provides for an integrated meter body with a thickness 68 that is close to the width of the test strips themselves. In this slim fromfactor, when the test strip is ⅜" wide, the integrated meter body would have a thickness 68 that is close to half-an-inch.

The test strip feeding mechanism 36 as has been described earlier with the help of FIGS. 2B and 2D is equally applicable to this slim form-factor. The only difference between this slim form-factor, as illustrated in FIG. 5, and the form-factor illustrated in FIGS. 2B,C and D earlier is that the meter body 12 and thus the meter display 32 is preferably positioned vertically over the test strip magazine 12.

FIG. 5 also shows the position of the test strip push plate 36A as part of the test strip feed mechanism 36 on the top of the meter body 12 and the extension of the test strip 16 with the sample intake-end 16B on the right side of the body ready for the blood sample intake.

In such a slim form-factor of the integrated meter, the notional outer dimensions are: a height 67 of approximately 2.5", including a height 65 of 1.5" for the test strip magazine and a height 66 of 1" from the meter body including the meter display; a width 69 of approximately 2", including a width 63 of magazine 12 for a test strip that is 1.5" long; and a thickness 68 of approximately ½", based on using a test strip that is ⅜$^{th}$ inch wide. The 1.5" height 65 of the test strip magazine 12 would support a test strip capacity of fifty test strips.

If the magazine capacity is for 25 test strips, and thus the magazine 12 is 0.75 inch in height 65, the height 67 of the integrated meter would be approximately 1.75". Such a slim form-factor integrated meter with a single magazine, more or less would resemble a size smaller than a wallet in the overall dimension and thus, it is believed, would be very convenient and easy to carry in the personnel possession of any class of users.

Used Test Strip Storage Compartment 62

FIG. 5 also shows the position of a used test strip storage compartment 62. When a user is on the move and tests his blood glucose, with the integrated meter 10, he/she would have a small immediate problem of discarding the used test strip. To alleviate this immediate problem, the integrated meter 10 of the embodiments herein may provide for a used test strip storage compartment 62 of width 64 as shown in a simplified illustration in FIG. 5.

The used strip compartment 62 depending upon the size of the magazine 12 may be attached or included with the magazine 12 itself. The used test strip compartment 62 may be positioned at the bottom of the magazine 12 or it may also be positioned at the back end of the magazine 12, as shown.

The used test strip compartment 62 can store a small number of used test strip until the compartment can be emptied in a suitable container such as a trash bin. The size of the used test strip compartment 62 may store as many as 10 to 20 used test strips or it may store more based on the design and aesthetics of the overall design of the integrated meter.

Test Strips 16

Test strips that are used in a blood glucose measuring device are prior art as are the blood glucose measuring devices themselves. Each manufacturer of a blood glucose measuring device manufactures and markets test strips that work only with their blood glucose measurement device.

Test strips are used as a supply and are consumed on a regular basis by those with Type 1 or Type 2 diabetes to measure their blood glucose levels many times in a day. Therefore, a prior art manufacturer of the blood glucose measuring device, heavily discounts or gives away for free the glucose meter itself and makes money by selling the test strips for their meter.

Industry has developed different formats of test strips themselves. In one format, the blood intake is at the end of the strip, in another format, the blood intake is on the side of the strip, and in yet another format, intake of the blood sample is in on the top of the test strip.

The size of the test strips may be and are different for each format and also different between test strips of different manufacturers using the same format of the test strip. As a simplified illustration, a test strip manufactured by Roche Diagnostic Corporation for use in Accuchek meters is 1.5 inches long and ⅜" wide and a test strip manufactured by Arkray Corporation for use in Glucocard® meters is 1⅛" long and is ¼" wide.

The embodiments described for, an integrated blood glucose meter 10, test strip magazine 10A and related embodiments herein may be adapted for use with any type of test strip format and test strip size.

In some test strips, such as Accuchek test strips, the blood sample intake-end, in thickness of the test strip, is slightly more than the rest of the test strip to accommodate the thickness of the sample intake wick gauze and its protective cover. While in some other test strips such as from Arkray, the thickness at the interface-end in their test strip is slightly less than the rest of the test strip.

These test strips by prior art manufacturers may be adapted to provide a uniform thickness on either the entire length or a major part of the test strip length to be able to closely stack on top of each other to provide a stack for the test strip magazine. As a simplified illustration, a uniform thickness of the test strip may have a recess or a reduced thickness to accommodate the sample intake-end thickness, making for a uniform thickness along the major length of the test strip.

Alternatively the test strips may be custom made for the embodiments herein and may have a custom length, custom width, and custom thickness for use in the tests strip magazine 10A and the integrated glucose measuring device 10 of the embodiments described herein.

One custom aspect of the test strips may be where the electrical interface-end 16A is positioned on the test strip 16, so that the interface-end 16A would interface with the electrical contact prongs 34 of the meter. Another custom aspect may be the thickness of the test strip that would make the test strips to uniformly stack up and a test strip on a top end of the stack is pushed out for use. Another custom aspect may be the width and the length of the test strip. Since the test strips are not manually handled using the embodiments herein, that would provide for yet smaller integrated glucose measuring device 10 of the embodiments herein.

Industry uses electrochemical technology in the test strips for the blood glucose measurement. During the prior art manufacturer of the test strips, using the electrochemical technology, a reagent is provided in the sample intake-end of the test strip. At the time of using a test strip with a blood glucose meter, the reagent in the test strip chemically reacts with the whole blood sample to provide an electrical signal that is proportional to the glucose in the whole blood.

This reagent may deteriorate during storage of the test strips. Hence prior art provides for a shelf life of the test strips in an air tight sealed test strip storage container. That shelf life may be of the order of a year, more or less. Further, the prior art provides that the individual test strip that is retrieved from an air tight storage container be used as soon as possible in the glucose meter to avoid deterioration of the chemical reagent during extended air exposure of the test strip. Extended air exposure of the test strip may deteriorate the reagent and thus may affect the accuracy and or consistency of the blood glucose reading that would be obtained with such test strips.

The test strip magazine of the embodiments and the test strip stack of the embodiments herein are adapted to minimize air exposure of the test strips in the magazine. Hence the test strip magazine or the test strip stack packaging for use in a magazine is stored in an air tight container until the test strip magazine or the stack is used with the integrated blood glucose measuring devices of the embodiments herein.

Further, the test strip magazine itself is made air tight during the use of the magazine in the integrated devices. The magazine is made air tight by air sealing the top end of the stack and the openings that are used to push an individual test strip on the top of the stack out of the magazine. These areas of the magazine in these openings may be air sealed by using felt padding as a sealing material.

As a simplified illustration of pressure felt padding that may be used in the test strip magazines of the embodiments herein is what had been used in prior art cameras and prior art roll of films, before the advent of the digital cameras. In these prior art cameras and film rolls, the inside of the camera and the roll of the film is made light impervious by using padding in the camera compartment cover and the padding used in the film roll opening.

Test Strip Packaging 70

FIGS. 6A and 6B illustrate packaging of the test strips 16 for the embodiments herein. With the packaging of the test strips along with the use of a test strip magazine 12 of the embodiments described herein, efficiently packaging a large number of test strips and efficiently retrieving a single test strip from the packaging, it is believed, is much improved compared to the prior art.

Prior art test strips are loosely packaged in a cylindrical container. A typical prior art test strip container is cylindrical in shape and is sized to store maximum of 50 test strips and is about 1.25" wide in diameter and 1.5 inches in height.

In prior art, at the time of the use where an individual test strip is needed, the container lid is opened to retrieve an individual test strip from the container. In prior art, retrieving of test strips, one at time, from the container is a cumbersome effort, as the test strips tend to stick to each other and some manual dexterity using fingers is required to retrieve a single test strip from the storage container.

A prior art, introduced in 2008 under the brand name ACCU-CHEK®, by Roche Diagnostic Corporation, has attempted to address this difficulty of retrieving a single test strip from a loosely packaged test strip container by using a drum design packaging of test strips.

That is, the ACCU-CHEK® Compact Plus model makes a prior art packaging of tests strips that is in the form of a drum. The drum packaging stores a number of test strips in a circular drum about one inch in diameter and one inch high. Based on the size of the test strips and the diameter of the drum, the number of test strips in the drum is limited to be seventeen test strips. The ACCU-CHEK drum is inserted in the back of the ACCU-CHEK meter by removing a drum compartment cover and inserting the drum in place. The drum is operated by an electrical motor inside the meter.

In the prior art Accu-chek® model, a push button switch on the front side of the meter turns on the meter, electrically energizes the motor to rotate, and positions a test strip in the meter with the sample intake-end sticking out. That is, a single test strip is pushed out of the drum and feeds one test strip at a time into the meter. This drum arrangement of test strips has limited the number of test strips in a single drum packaging to seventeen in such a packaging design.

After the sample intake and a reading display, the same push-button switch on the meter is used by the user to eject the test strip. This design, using a drum and an electrical motor to operate the drum, has not only increased the thickness of the meter to more than an inch but has also made the operation of the meter noisy based on review comments on the Internet.

Another prior art under the brand name Ascensia Breeze 2® by Bayer Corporation, has also attempted to address this difficulty of retrieving a single test strip from a loosely packaged test strip container by using a daisy wheel disc design packaging of test strips.

That is, the Breeze 2® makes a prior art packaging of tests strips that is in the form of a daisy wheel disc. The daisy wheel packaging stores a number of test strips in a circular daisy wheel pattern that stores ten test strips. Thus, the daisy wheel design packaging of test strips in the daisy wheel disc is limited to be ten test strips.

The daisy wheel disc is inserted in the back of the meter by removing a compartment cover and inserting the daisy wheel disc in place. By pushing a large mechanical switch at the bottom of the meter and then separating the large switch from the meter body, the daisy wheel is rotated inside the meter body and a new test strip from the daisy wheel is inserted is the meter and the sample intake-end of the test strip is exposed out of the meter body. After the sample intake and a reading display, another push-button switch on the meter is used by the user to eject the test strip.

As described in the embodiments herein related to packaging of the test strips, a test strip package that is very efficient in packaging a large number of test strips can be purchased from a pharmacy and then dropped or inserted inside the test strip magazine. As illustrated with the help of FIG. 6A, the test strips 16 are packaged in a package 70 for use with the magazine 10A as described in the embodiments herein.

This form of test strip packaging 70 for use with a test strip magazine chamber 12 of the embodiments herein provides for a multi-fold increase in the quantity of test strips that can be used in the integrated meter 10 than any prior art.

In the slim form embodiment as had been described earlier with reference to FIG. 5, when the test strip magazine stores 50 test strips, that provides for a three-fold increase compared to Accuchek meter with seventeen test strips and five-fold increase compared with Bayer Breeze meter that stores ten test strips.

When a magazine with two chambers to store test strips is used, as illustrated in FIG. 2A, that provides for an almost six to ten fold increase in the quantity of test strips accessible to a meter user, without having to replenish or reload the test strip magazine.

As illustrated in FIG. 6A, a pack 72 of test strips has test strips 16 that are rectangular in shape with an interface-end 16A and a sample intake-end 16B. The test strips 16 are stacked on top of each other in a stack 72 with each test strip aligned in the same orientation of the ends within the stack. The stack 72 is held together by a removable test strip wrapper 74.

Automated packaging techniques of packaging items in a stack and then binding them with a removable wrapper are prior art. These prior art packaging techniques may be adapted to package the test strips in a stack for use in the test strip magazine of the embodiments herein.

A single stack package 70 of test strips 16 may have a quantity of one of, twenty, twenty-five, thirty, thirty-five, forty or fifty test strips in one stack 72 of test strips. That yields a test strip package 70 stack height that is less than or of the order of an inch and a half based on an assumed test strip thickness of 1/32".

Each such stack 72 of test strips of the test strip package 70 is bound or held together by a wrapper 74. The test strip stack wrapper 74 may be made of smooth paper. It may be a waxed paper or some other suitable material such as a light weight plastic ribbon that can be pulled loose for removal from around the test strip stack. The wrapper 74 paper may be approximately half the length 75 of the test strips and the wrapper 74 may be positioned in the middle of the length of the test strips.

Assuming a test strip length of 1.5 inches, the wrapper 74 may be close to 0.75 inch wide. The wrapper 74 may be more or less than this length dimension and test strip 16 length itself may be less or more than the test strip length dimension mentioned above. It should be understood by those skilled in the art of packaging that these are notional dimensions illustrative of the embodiments herein.

The wrapper 74 ends may be glued or fused with each other. There is a loose folded access flap 76 on the top for the wrapper 74. The loose flap 76 facilitates removal of the wrapper 74 from the stack 72 by pulling at it. The wrapper 74 is intended to be removed after the test strip package 70 is dropped in the magazine 12, enabling loading of a test strip magazine without handling individual test strips.

The wrapper 74 is preferably made of a thin and smooth material such as similar to Mylar®, a metalized nylon. Such characteristics of the wrapper 74 enable the wrapper 74 to be easily pulled loose from the stack 72, after the package 70 has been dropped inside a magazine.

Sometimes the terms "test strip stack" and "test strip stack package" identified by items 72 and 70 in the FIG. 6A may have been used interchangeably. However, the term "test strip stack" 72 refers to the stack of test strips without the wrapper 74 and the term "test strip package" 70 is used for the test strip stack bound together by the wrapper 74.

The magazine 12 design may permit either a top-loading or a bottom-loading magazine. However, in some embodiments, a bottom-loading magazine is preferred as the top end of the magazine is engineered to be attached to or integrated with the meter. In such an embodiment, a test strip package 70 as described above may be purchased and used with a magazine that is permanently affixed to the meter.

In another embodiment, the magazine itself may be purchased preloaded with a stack of test strips such that no wrapper is needed to be removed and where the magazine is then attached to the meter.

This manner of packing the test strips 16 in a stack 72 makes for a convenient and compact storage of the test strips for a user. Each test strip stack package 70 may be individually sealed in air tight packaging using foil material packaging.

As illustrated in FIG. 6B, the package 70 of test strips is stored in an air tight container 78. The container 78 may be sized to store a plurality of test strip packages 70. Since the stacks are rectangular, the container is also shaped rectangular, and may store multiple stacks of test strips.

Test Strip Count Logic 80

In some embodiments, the test strip count and display logic 80 described here may be used with the prior art glucose meters without the use of the meter that is integrated with a test strip magazine that has described earlier with the help of FIGS. 2A-2D. In other embodiments the test strip count logic 80 may be used with the meter that is integrated with a test strip magazine as has been described earlier herein.

Both of these logic implementations provide for logic and a corresponding meter display on the initialized supply of test strips available and the quantity of test strips available or used. The embodiments are illustrated with the help of FIGS. 7A and 7B.

Figure 7A:
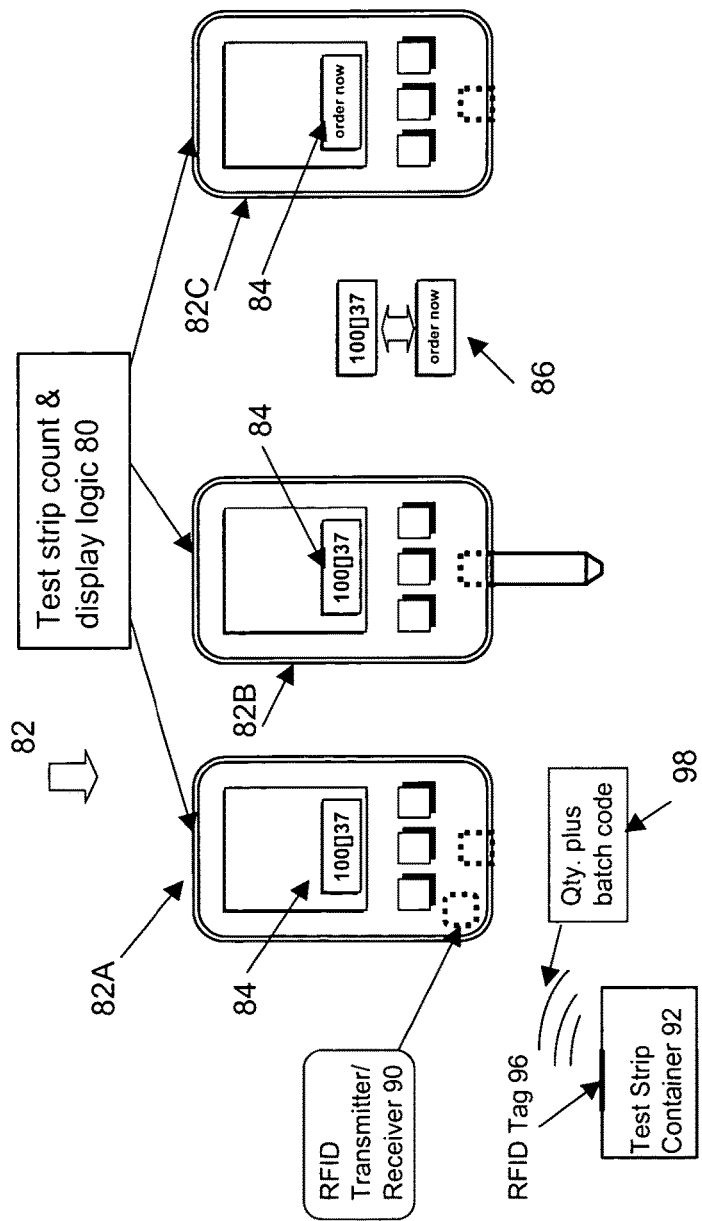

As illustrated with the help of FIG. 7A, a test strip count and display logic 80 may be used in a prior art blood glucose meter 82. As illustrated in FIG. 7A, three views of meter 82 are shown. The view 82A shows the meter with a RFID Transmitter/Receiver 90. The view 82B shows the meter 82 with a test strip inserted in the meter and the view 82C shows the meter powered up but without a test strip. In each of these three views, a display window 84 as part of the meter display screen is shown.

The display window 84 shows two numerical values. The first of these display 84 values, shown as equal to 100 as a illustration, represents the stock quantity of test strips that a user has in his/her possession. This may represent a 30 day supply or a 90 day supply based on the order size of the prescription. Typically three strips are used in a day, making a box of 100 strips as a one month supply and three boxes totaling 300 as a three month supply. The second numerical value on the display 84 shows either the test strips already used from the stock value or the remainder of strips in the stock value.

The logic 80 is initialized with the stock quantity value of the test strips. This may happen in different ways. In one of the ways, a test strip container 92 has a RFID tag 96 with a number which corresponds to the quantity of test strips in the container 92. The meter 82A with the RFID logic 90 is activated by a user and the stock value is automatically read from the RFID tag 96. In another way, the stock value is selected from a set of fixed numbers such as fifty, one hundred, one hundred fifty, two hundred, two hundred fifty, and three hundred.

The prior art meters need to be calibrated for a specific batch of test strips to account for variations in the test strip manufacturing process. To provide for the calibration of the meter for a batch of test strips, prior art industry provides for three different ways. Each batch of test strips has a code number representing the batch, and that number needs to be entered in the meter. It may be entered manually. However the industry has found users make mistakes in that and have discovered better ways to code the meter. One of these ways is providing for the code in a circuit chip key. The key that comes packaged with a container of test strips from a given batch needs to be inserted in the meter for coding the meter and for the meter to operate.

To even remove this human step for the user to perform, the prior art industry has developed a no-coding technology, where the code is made a part of the each individual test strip and is read by the meter each time a test strip is inserted, thus avoiding any human errors in the coding process.

The RFID logic 90 equipped-meter 82 as described above provides a fourth way to code the meter. The RFID tag 96 may contain, in addition to test strip quantity, a batch code 98, which will be read at the same time as the test strip quantity in the test strip container. As a simplified illustration, the RFID tag may contain a numerical value 1009345, where the 100 represents the quantity of test strips, 9 is the separator and 345 is the batch code for this batch of test strips.

This fourth way of coding the meter using a batch code 98 in a RFID tag 96 on the test strip container 92, may be used in lieu of any of the prior art coding for a given batch of test strips, or it may be used in addition to some of the prior art ways already described. As a simplified illustration, the RFID method of coding may replace the prior art key chip method.

Alternatively, the RFID method may be used in addition to, or in combination with, the individual test strip code method or the "No Coding" technology method as the industry calls that. Thus, the RFID method would provide for a double check on the code number as the two would be the same number, one on the test strip and the other on the container, retrieved by the RFID receiver inside the meter body.

Now returning to the test strip quantity, as each strip is used in the meter 82B, the second value on the display 84 is either incremented or decremented. The logic 80 computes the quantity of test strips that have been used out of the stock count value and if the stock is below a threshold, the display 84 shows a legend "order now". The display 84 may flash 86 between the two display values, whenever the meter 82B is used with a test strip or when the meter is powered 82C.

Figure 7B:
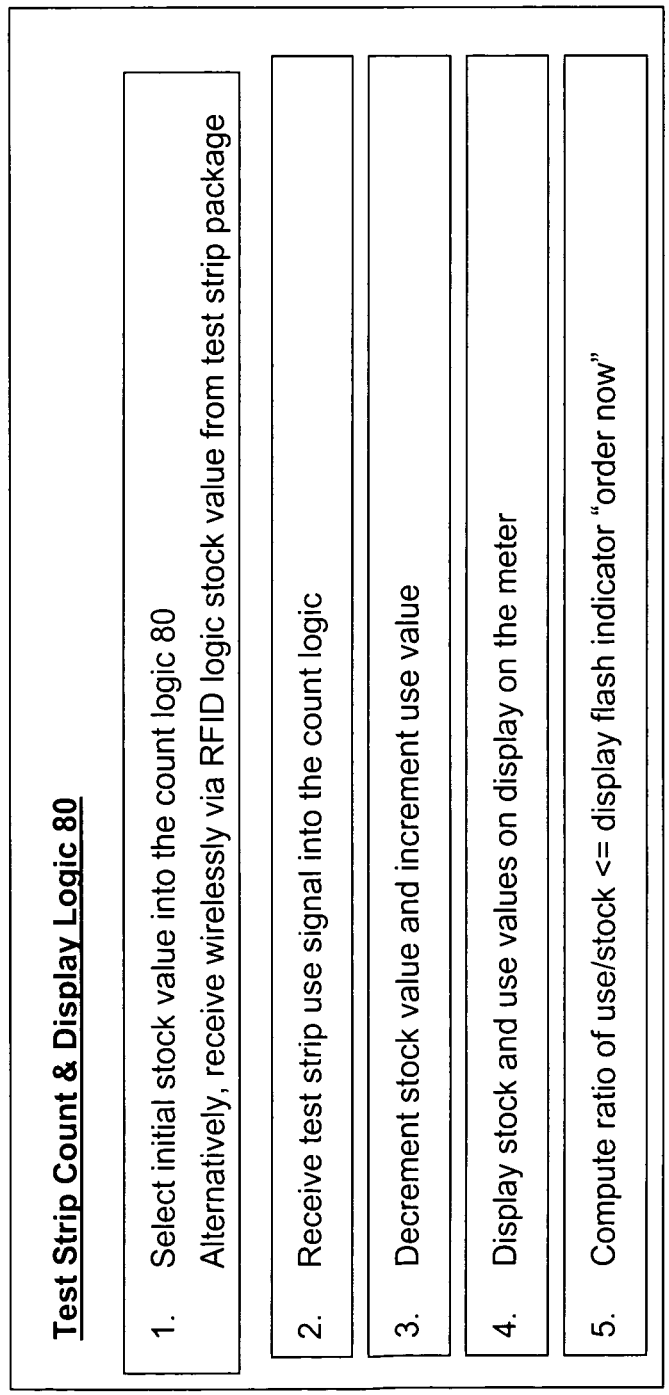

The test strip count and display logic 80 functions are illustrated with the help of FIG. 7B. These functions are:
1. Logic helps a user select an Initial Stock Value into the Count Logic 80 by selecting a single value from a list of stock values. Alternatively, logic 80 receives wirelessly via RFID logic 90 a stock value from Test strip package 92.
2. Logic 80 receives a test strip use signal into the count logic 80.
3. Logic 80 decrements stock value and increments use value.
4. Logic 80 displays stock and use values on display 84 on the meter 82.
5. Logic 80 computes ratio of use/stock and if below a threshold, display flash indicator that flashes between "order now" and the count display.

As illustrated in FIG. 7A test strip count and display logic 80 is provided in the meter body 82. The logic 80 enables sensing insertion of a test strip, input of a sample and reading following that and thus sense of a use of a test strip. This signal at either stage from the prior art meter logic or some combination of stages may be sent to a count logic 80 of the embodiment herein.

The count logic 80 maintains an initial count and an as used count of the test strips by decrementing the initial count. The display 84 displays a number with both of these values. As a simplified illustration the display may be 100/42, indicating to the meter user that of the stock of 100 test strips, either 42 remain or 42 have been used. The count logic may also provide visual advisory at each use of the test strip, if the as used count exceeds or falls below a threshold alerting the user to order a fresh supply of test strips Sometimes the supplies are dispensed in a month stock and sometimes in a 3 month stock. Hence the count logic may maintain stock and as used count in either of these base periods. The initial stock value is initialized by the user or may be preprogrammed to certain specific values to be selected by the user. For example the initial stock value may be 25, 50, 100, 150, 200, 250 or 300 etc, from which one value may be selected by the user.

With reference to FIGS. 7A and 7B, a test strip count and display logic 80 has meter 82. The logic 80 may be integrated with a meter that is integrated with a test strip magazine as has been described in the embodiments herein. The logic 80 is then made part of the meter 12 logic and the display 84 is made part of the meter display 32. The meter may be programmed with features that may enable the user to select a desired form of test strip used display, such as to show either test strips remaining or the test strips used based on user preferences and protocols and conventions in different countries.

The count logic 80 is initialized or is reset with the help of a switch (not shown) on the meter 12. When reset, the display 84 may display two different count number displays X and Y, where the X may display the capacity size of the magazine and Y may display, the number of test strips remaining in the magazine after each strip use in the meter. That is, the number Y is decremented after each test strip use from the magazine in the meter.

As a simplified illustration, if the magazine stores 100 test strips, the number X=100 would be displayed. If the magazine stores a different capacity, then that number would be displayed. The number Y would display starting at 0 and increment by one, each time a test strip is used and emptied from the chamber of the magazine. In the simplified illustrations here, "X" has been used to indicate a stock quantity or magazine size, and "Y" has been used to indicate the number of test strips remaining in the magazine or from the stock quantity.

The logic 80 may keep relative count of both numbers and may display advisories as the magazine is used or emptied. These advisories may include ten strips remaining, five strips remaining etc. to provide a visual and or aural advisory and indication regarding the status of the number of test strips in the magazine.

With magazines with dual chamber with a test strip stack in each chamber, the logic 80 may keep a dual count and display a dual count for each magazine. As a simplified illustration of this embodiment, the number X may display 50/50, and the Y display may display 50/30. The meter provides for user option to use either a test strip from a left chamber or a right chamber of the magazine. The use number Y may display a number such as 22/34, as an indication that 22 test strips and 34 test strips remain in the left and right cambers respectively. Alternatively, the Y display number may display either the number of test strips used or remaining depending upon the human perception and protocol in each country.

The software/firmware for such a count logic is considered prior art, except its specific use with a meter with a test strip magazine as described herein. The logic 80 already electrically senses the insertion of a test strip in the meter either from the left or the right chamber of the magazine. This sense signal is used to input to a count-logic for each chamber. The numbers are reset individually for each chamber as the test strip stack in each chamber of the magazine is inserted.

As a simplified illustration if the left chamber is empty and the right chamber has 30 strips, then X=50/50 and Y=0/30 signaling that the left chamber is empty and the right chamber has 30 test strips remaining. When the left chamber is inserted a fresh test strip pack, the Y=50/30.

If the test strip stack package contains 25 test strips, the number X=25/25 and Y=25/25 are the initial setting. It is also possible to put different capacity test stack packs in each chamber. For example, a test strip pack of 25 strips is inserted in the left magazine and a test strip stack of 50 test strips is inserted in the right magazine. Then the X=25/50 and Y=25/50 as an initial reading before the test strips start getting used from either chamber.

The initial X values may be manually initialized or automatically sensed by the meter logic with the help of a test strip package stack-height sensor, in each of the magazine chambers. The science of a sensor for depth or height of filling a chamber is considered prior art and may use sensors that may be based on weight of package 72 or degree of relative light/darkness in the chamber.

As has been described above with the help of FIG. 7A, an RFID function 90 in the meter may be used to read batch quantity and batch code 98 from an RFID tag 96 on the test strip pack 92. The Test Strip Pack Batch Code & RFID Logic 85 functions/logic is illustrated with the help of FIG. 7C. These functions are:
1. Place a new Test Strip Pack near the RFID adapted meter 82 and manually activate on the meter, a new test strip batch function.
2. The RFID logic 85 in the meter reads the RFID tag 96.
3. The RFID logic 85 parses the quantity and batch code 98 and store them in the meter memory.
4. The logic copies the quantity to quantity logic and the code to the code logic.
5. A new test strip is used or inserted in the meter from the magazine.

6. The test logic uses the stored code.
7. If the test strip is of the type that has the code on the test strip itself, the logic compares the two codes and verifies that the codes match.

A blood glucose meter with a test strip use count system has a meter logic that operates the meter including functions of (i) sensing insertion of strip, (ii) sensing intake of blood sample and (iii) yields a measurement. The test strip count logic and a test strip count display are in the meter. The meter logic is adapted to send a signal, when one or more of the meter functions are sensed, to the count logic. The count logic on receiving the signal, maintains a strip use count in the count logic and the count logic displays the test strip use count using the count display on the meter.

The count logic maintains two count values, one for the test strip stock quantity at hand with a user, and the other count for either how many strips have been used or remain from the stock quantity. The count logic displays on the count display side by side, the stock count value and the use count value.

The count logic computes a remainder stock value, each time a count use value is updated and if the remainder falls below a threshold, the count logic via the count display annunciates a legend "order new stock", or annunciates an alternate flashing display with count values and "order new stock" legend. The display is annunciated each time the meter is used with a test strip or just powered-up.

The stock value is initialized with a standard quantity of the package from a list of 25, 50, 100, 200, and 300.

The meter may also be adapted with a low power RFID transmitter receiver electronics and logic limited to operate within a distance of less than a foot. The RFID logic is manually operated once when a new stock of test strips is received and placed in the close vicinity of the meter and the logic reads the RFID tag on the stock supply to automatically read and update the stock count value in the count logic.

A test strip package has an RFID tag with a tag number is attached to the package, where the number in the tag corresponds to the quantity of test strips in the package. The number in the tag in addition corresponds to a batch number of the test strips for use in calibrating the meter for a given batch of test strips.

The RFID tag is removable from the package, when the tag number has been read by a meter equipped with RFID logic. The RFID tag is placed on a flap of the test strip package and the flap is removed to remove the RFID tag, when the tag number has been read by a meter equipped with the RFID logic. The RFID transmit energy sized to transmit a distance less than a foot from the receiver.

In summary of the test strip package feature, test strip magazine feature and the meter feature, a meter integrally combined with a test strip magazine storing test strip packs has been described above with the meter logic and a sensor to provide a visual indication on the meter display on the quantity of test strips loaded in the magazine chambers and the count status of test strips remaining or used from each of the individual chambers of the test strip magazine. The RFID logic can read both the batch quantity and the batch code from the RFID tag. Thus providing valuable human-factors features to the diabetic user of the integrated meter device 10 of the embodiments herein.

Mode of Operation

As has been illustrated with the help of FIGS. 2A-2D, a user first examines the test strip magazine 10A of the device 10 to see the clear plastic magazine 12A and 12B and observes that there is a supply of test strips in the magazine 10A and which magazine 12A or 12B he/she would like to use.

Then a user uses the lancet 10D to arm and deploy to prick his/her finger. Then the user turns the device 10B around and slides the lever 36A of mechanism 36 to deploy a test strip 16 from either left or right chamber. In some embodiments, the lancet 10D may be mounted in the front and side of the meter 10B, thus avoiding this step of turning the meter 10B around.

The test strip 16 is deployed and the meter 10B is activated automatically when the electrical connection 34 is made between the test strip 16 and the meter 30. The user touches the finger to test strip end and waits for the meter to provide a reading. The user pulls and removes the test strip 16 and discards it. The user presses a switch 40 to examine the readings via a graph. Alternatively as in embodiment as shown in FIG. 2C, the test strip 16 is manually pulled from the magazine 10A and then manually inserted in the slot 46 of the meter body 30.

When the test strip magazine 10A is empty of test strips, the lid at the bottom of the magazine may be opened to provide access to the inside of the magazine and stacks of the test strips may be dropped in the magazine 10A and the lid with the spring would be closed.

The meter 10B may also include memory and logic to store and display a daily and a weekly graph of the blood glucose readings on the display of the meter. The logic would be built in or programmed in the integrated circuit chips that would be used in the meter 10B.

Prior art advances in miniaturization of the electronic devices make such features possible in small electronic devices as in meter device 10B. A bar graph may be shown for a day or a week, along with horizontal lines indicating desirable and mean blood glucose values. In prior art, such analysis was done via porting the data from the meter device 10B to a computer with the software to be able to receive and analyze such data. Having logic and memory in the device 10B enables that feature to be available anywhere and anytime or when a reading is taken with the device 10.

Method of Operation

As illustrated in FIG. 4, a method for using the device 10 has the following steps where all the steps may not be used or used in the order specified:

At step 100, integrating a test strip storage magazine 10A with a blood glucose meter 10B.

At step 102, integrating a test strip feed mechanism 36 from the storage magazine 10A with the blood glucose meter 10B.

At step 104, integrating a lancet mechanism 10D with the blood glucose meter 10B.

At step 106, enabling releasing a test strip and automatically activating meter, when test strip connects to meter contacts.

At step 108, enabling using the deployed test strip for blood intake from the finger.

At step 110, enabling reading a blood glucose value from the meter.

At step 112, enabling activating a meter switch to display a graph with the current reading.

At step 114, enabling inserting a test strip storage magazine into the meter.

At step 116, enabling removing and replacing a used magazine with a new magazine.

At step 118, integrating a dual test strip feed mechanism from the dual storage magazine for use with the meter.

As Illustrated in FIG. 6C, a method for packing test strips is described. The test strips are rectangular shape with an electrical interface-end and a sample intake-end has the following steps, where all the steps may not be used or used in the order specified.

At step 120, stacking the test strips on top of each other in a stack with each test strip aligned in the same orientation of the ends within the stack.

At step 122, holding the stack together by a removable test strip wrapper.

At step 124, packing the test strips in the stack with one of 20, 25, 30, 35, 40, or 50 test strips in one stack, with a stack height that is less than or of the order of less than an inch and half based on test strip thickness of substantially 1/32".

At step 126, storing the stack in an air tight container for removal there from, inserting the stack in a test strip magazine for use with a blood glucose meter.

At step 128, enabling removal of the stack from the air tight container, enabling insertion of the stack in a test strip magazine and enabling removal of the strip wrapper for use of the stack of test strips with a blood glucose meter.

At step 130, sizing the container to hold multiple stacks of test strips.

As illustrated in FIG. 8A, a method for a test strip use count system in a blood glucose meter, has the steps, where all the steps may not be used or used in the order specified:

At step 132, operating by meter logic the meter functions including that of (i) sensing insertion of strip, (ii) sensing intake of blood sample and (iii) yields a measurement.

At step 134, having a test strip count logic and a test strip count display in the meter.

At step 136, adapting the meter logic to send a signal, when one or more of the meter functions are sensed, to the count logic.

At step 138, receiving the signal by the count logic, and maintaining a strip use count in the count logic and displaying by the count logic the test strip use count using the count display on the meter.

At step 140, maintaining by the count logic two count values, one for the test strip stock quantity at hand with a user, and the other count for either how many strips have been used or remain from the stock quantity.

At step 142, displaying by the count logic on the count display side by side, the stock count value and the use count value.

At step 144, computing by the count logic a remainder stock value, each time a count use value is updated and if the remainder falls below a threshold, the count logic via the count display annunciates a legend "order new stock", or annunciates an alternate flashing display with count values and "order new stock" legend.

At step 146, annunciating the display each time the meter is used with a test strip or just powered-up.

At step 148, initializing a stock value with a standard quantity of the package from a list of 25, 50, 100, 200, and 300.

As illustrated in FIG. 8B, a method for a test strip use count system and batch code using an RFID logic in a blood glucose meter, has the steps, where all the steps may not be used or used in the order specified:

At step 150, adapting the meter with a low power RFID transmitter receiver logic limited to operate within a distance of less than a foot;

At step 152, operating manually the RFID logic once when a new stock of test strips is received and placed in the close vicinity of the meter and the logic reads the RFID tag on the stock supply to automatically read and update the stock count value in the count logic.

At step 154, attaching an RFID tag with a tag number to the package, the number in the tag corresponds to the quantity of test strips in the package.

At step 156, making the number in the tag in addition corresponds to a batch number of the test strips and calibration coefficients for the batch.

At step 158, making the RFID tag removable from the package, when the tag number has been read by a meter equipped with the RFID logic.

At step 160, placing the RFID tag on a flap of the test strip package and the flap is removed to remove the RFID tag, when the tag number has been read by a meter equipped with the RFID logic.

At step 162, sizing the RFID transmit energy to transmit a distance less than a foot from the receiver.

In summary, the preferred embodiments are on a blood glucose measurement device 10 that integrates the measurement test strip storage 10A and the meter 10B in a single compact device, enabling test strips to be stored, retrieved and fed into the meter without being touched by the human in a single action.

In another embodiment, a compact version of the lancet mechanism 10D is attached to an end of the meter 10B body, providing all the three elements, lancet 10D, test strips 10A and the meter 10A to be integrated in a single compact device, that is believed, would be easy to carry, easy to store in personal possessions, and easy to use many times in a day.

While the particular invention, as illustrated herein and disclosed in detail is fully capable of obtaining the objective and providing the advantages herein before stated, it is to be understood that it is merely illustrative of the presently preferred embodiments of the invention and that no limitations are intended to the details of construction or design herein shown other than as described in the appended claims.

The invention claimed is:

1. A test strip packaging apparatus for packaging test strips for use with a blood glucose meter, comprising:
   test strips, where the test strips have an electrical interface-end and a blood sample intake-end, and wherein the electrical interface-end and the blood sample intake-end of the test strip are positioned on opposite ends of the test strip;
   the test strip packaging apparatus comprises the test strips in a stack on top of each other in a horizontally oriented stack, wherein each test strip is positioned within the stack with the interface-end and the sample intake end of the test strips aligned in the same direction in the stack;
   the test strip packaging apparatus is configured to hold the stack together by a removable test strip wrapper, wherein the removable test strip wrapper encircles the stack and has two ends, and wherein the two ends of the wrapper are affixed to each other by an adhesive;
   the test strip packaging apparatus is configured for inserting the stack inside a test strip magazine.

2. The pack of test strips as in claim 1, comprising:
   the stack has quantity of one of 20, 25, 30, 35, 40, or 50 test strips in one stack.

3. The apparatus as in claim 1, comprising:
   the stack of test strips is stored in an air tight storage container before insertion of the stack in the test strip magazine for use with the blood glucose meter.

4. The apparatus as in claim 1, comprising:
the strip wrapper has a free-end on one of the two ends, wherein the free-end is used to pull on the wrapper to remove the strip wrapper from the stack after the stack has been positioned inside the test strip magazine, thereby the magazine is replenished with the stack of test strips, without a user individually handling the test strips.

5. The pack of test strips as in claim 3, comprising:
the container is sized to store a plurality of stacks.

6. A method for packaging test strips in a test strip packaging apparatus, for use with a blood glucose meter, comprising the steps of:
providing a test strip that has an electrical interface-end and a blood sample intake-end, and wherein the electrical interface-end and the blood sample intake-end of the test strip are positioned on opposite ends of the test strip;
stacking the test strips by the test strip packaging apparatus in a stack on top of each other in a horizontally oriented stack, wherein each test strip is positioned within the stack wherein the interface-end and the sample intake end of other test strips are aligned in the same direction in the stack;
holding the stack together in the test strip packaging apparatus by a removable test strip wrapper, wherein the removable test strip wrapper encircles the stack and has two ends, and wherein the two ends of the wrapper are affixed to each other by an adhesive; and
the test strip packaging apparatus is configured for inserting the stack inside a test strip magazine.

7. The method as in claim 6, comprising the steps of:
packing the test strips in the stack with one of 20, 25, 30, 35, 40, or 50 test strips in one stack.

8. The method as in claim 6, comprising the steps of:
storing the stack in an air tight container and removing the stack from the container for inserting the stack in the test strip magazine for use with the blood glucose meter.

9. The method as in claim 8, comprising the steps of:
enabling removal of the stack from the air tight container, enabling insertion of the stack in the test strip magazine and enabling removal of the removable strip wrapper, enabling use of the stack of test strips with a blood glucose meter.

10. The method as in claim 8, comprising the steps of:
sizing the container to hold multiple stacks.

11. A test strip storage magazine for use with a blood glucose meter, comprising:
a test strip that has an electrical interface-end and a blood sample intake-end on opposite ends of the test strip;
the test strip storage magazine has two separate test strip storage chambers, wherein each storage chamber is configured for storing and stores a separate stack of test strips and wherein, in each of the test strip storage chambers the test strips in the stack are positioned within the stack, wherein the interface-end and the sample intake end of other test strips are aligned in the same direction in the stack;
the test strip storage magazine, wherein the electrical interface end of the test strip, in each of the chambers of the test strip storage magazine, is facing up to be accessible to be electrically interfaced with a separate blood glucose metering device;
the test strip storage magazine has an open end and a closed end and wherein the test strip storage magazine at the open end has an attachment mechanism, for attaching to the separate blood glucose metering device for electrically interfacing with the separate blood glucose metering device.

12. The device as in claim 11, comprising:
the magazine has an air tight removable cover, enabling the cover to be removed and the magazine to be attached to a test strip dispensing device for use with the blood glucose metering device.

13. The device as in claim 11, comprising:
a mechanism at the closed end of the magazine to push the stack of test strips up in the magazine;
lips at the open end of the magazine, to hold a top test strip in the stack in place, enabling the top test strip in the stack to be removed by sliding the test strip out and the next test strip in the stack to automatically position itself as the top test strip in the magazine for removal.

14. The device as in claim 13, comprising:
the closed end of the magazine has a removable lid to insert a stack of test strips in the magazine.

15. The device as in claim 11, comprising:
the magazine has a lever to push a top test strip out of a chamber for use with the blood glucose metering device.

16. The device as in claim 11, comprising:
each chamber is sized to stack quantity of test strips from 20, 25, 30, 35, 40, 45, or 50.

17. The device as in claim 11, comprising:
the magazine is made of clear plastic material for the loading of the magazine and remainder of the test strips, as the test strips are used in the magazine, to be visually ascertained.

\* \* \* \* \*